United States Patent
Mosesov et al.

(10) Patent No.: US 11,737,824 B2
(45) Date of Patent: Aug. 29, 2023

(54) MICROWAVE ABLATION PROBE

(71) Applicant: Biocompatibles UK Limited, Camberley (GB)

(72) Inventors: Oleg F. Mosesov, Maple Grove, MN (US); Daniel T. Kollmann, Andover, MN (US)

(73) Assignee: BIOCOMPATIBLES UK LIMITED, Surrey (GB)

( * ) Notice: Subject to any disclaimer, the term of this patent is extended or adjusted under 35 U.S.C. 154(b) by 270 days.

(21) Appl. No.: 16/988,174

(22) Filed: Aug. 7, 2020

(65) Prior Publication Data
US 2021/0038303 A1      Feb. 11, 2021

Related U.S. Application Data

(60) Provisional application No. 62/883,989, filed on Aug. 7, 2019.

(51) Int. Cl.
*A61B 18/18*      (2006.01)
*A61B 18/00*      (2006.01)

(52) U.S. Cl.
CPC ..... *A61B 18/1815* (2013.01); *A61B 2018/00035* (2013.01); *A61B 2018/00077* (2013.01); *A61B 2018/00577* (2013.01); *A61B 2018/1846* (2013.01); *A61B 2018/1861* (2013.01)

(58) Field of Classification Search
CPC ...... A61B 18/1815; A61B 2018/00035; A61B 2018/00077; A61B 2018/00577; A61B 2018/1846; A61B 2018/1861
See application file for complete search history.

(56) References Cited

U.S. PATENT DOCUMENTS

| | | | |
|---|---|---|---|
| 5,330,518 A * | 7/1994 | Neilson | A61B 18/1815 607/116 |
| 6,016,811 A | 1/2000 | Knopp | |
| 6,223,085 B1 | 4/2001 | Dann et al. | |
| 8,958,887 B2 * | 2/2015 | Hancock | A61B 5/065 607/101 |

(Continued)

FOREIGN PATENT DOCUMENTS

| | | |
|---|---|---|
| CN | 108670405 A | 10/2018 |
| EP | 4009897 A2 | 6/2022 |

(Continued)

OTHER PUBLICATIONS

International Search Report and Written Opinion for International patent application No. PCT/US2020/045440, filed Aug. 7, 2020, dated Feb. 5, 2021.

*Primary Examiner* — Linda C Dvorak
*Assistant Examiner* — Abigail Bock
(74) *Attorney, Agent, or Firm* — Faegre Drinker Biddle & Reath LLP

(57) ABSTRACT

Various aspects of the present disclosure are directed toward apparatuses, systems, and methods that may include a microwave ablation probe. The microwave ablation probe may include a feedline having an inner conductor, an outer conductor and a dielectric; and an antenna including a helical arm, the helical arm being electrically connected to the outer conductor of the feedline at a junction point, and a linear arm, the linear arm being electrically connected to the inner conductor of the feedline.

20 Claims, 12 Drawing Sheets

(56) References Cited

U.S. PATENT DOCUMENTS

| | | | |
|---|---|---|---|
| 2003/0195595 A1* | 10/2003 | Bolmsjo | A61B 18/1815 607/101 |
| 2007/0203551 A1* | 8/2007 | Cronin | A61B 18/04 607/101 |
| 2008/0266203 A1 | 10/2008 | Rossetto | |
| 2009/0082762 A1 | 3/2009 | Ormsby | |
| 2011/0077635 A1 | 3/2011 | Bonn | |
| 2011/0118723 A1 | 5/2011 | Turner | |
| 2012/0172862 A1* | 7/2012 | Brannan | A61B 18/18 606/33 |
| 2013/0072924 A1 | 3/2013 | Burgener | |
| 2014/0081254 A1 | 3/2014 | Rudue | |
| 2015/0038956 A1 | 2/2015 | Amabile | |
| 2016/0199130 A1 | 7/2016 | Belluomo | |
| 2019/0321097 A1* | 10/2019 | Cao | A61B 90/11 |
| 2021/0038303 A1 | 2/2021 | Mosesov et al. | |

FOREIGN PATENT DOCUMENTS

| | | |
|---|---|---|
| JP | 2008-272472 A | 11/2008 |
| JP | 2012-139495 A | 7/2012 |
| JP | 2014-531265 A | 11/2014 |
| JP | 2016-528987 A | 9/2016 |
| WO | 2021026471 A2 | 2/2023 |

\* cited by examiner

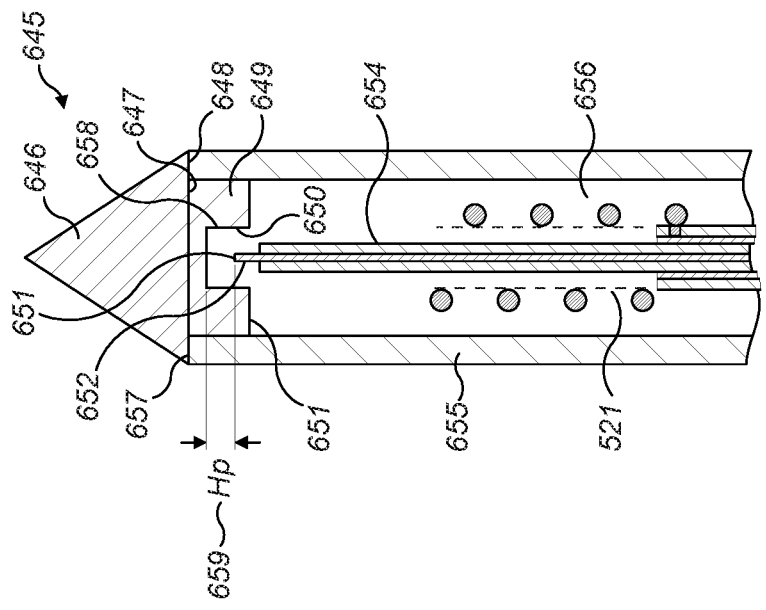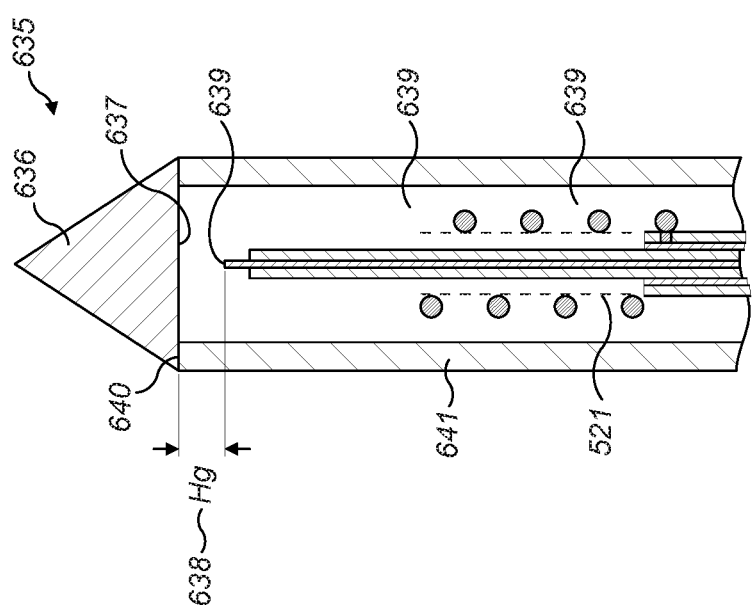

MICROWAVE ABLATION PROBE

CROSS REFERENCE TO RELATED APPLICATION

This application claims priority to Provisional Application No. 62/883,989, filed Aug. 7, 2019, which is herein incorporated by reference in its entirety.

BACKGROUND

In the treatment of diseases such as cancer, certain types of tissues have been found to denature at elevated temperatures. These types of treatments, known generally as hyperthermia therapies, typically utilize electromagnetic radiation to heat cancerous tissue to temperatures above 60° C. while maintaining healthy tissue at lower temperatures where irreversible cell destruction will not occur. Microwave ablation is one of such treatments utilizing electromagnetic radiation to heat tissue.

Microwave tissue ablation is a less invasive procedure than surgical removal and is preferred in many situations when tumors are difficult to remove by surgery, for example when the tumor is relatively small, disposed close to a relatively small organ, or disposed close to a major blood vessel. The approach has been used in organs such as the prostate, heart, and liver, where surgical removal of tumors may be difficult to perform.

In order to effectively plan and optimize the procedure, it is desired that the ablation device causes predictably sized and shaped volumes of ablation. For this reason regularly shaped, predictable ablation volumes are preferred, and it is particularly preferred to produce spherical, or near spherical ablation volumes. An ablation device with predictably sized and shaped ablation volumes simplifies the surgical procedures and reduces the undesirable medical complications.

The embodiments disclosed herein are directed to reduce the effect of the above mentioned issues associated with microwave tissue ablation devices. More specifically, the embodiments disclosed herein provide microwave antennas that may be used to produced regularly shaped, predictable ablation volumes, and to produce spherical, or near spherical ablation volumes.

SUMMARY OF THE INVENTION

Aspects of the invention are directed towards a microwave ablation probe include a feedline and an antenna. The feedline may have an inner conductor, an outer conductor, and a dielectric disposed there-between. The antenna may include a helical arm and a linear arm. The helical arm can be electrically connected to the outer conductor of the feedline at a junction point; the helical arm may further be extending in a distal direction from the junction. The linear arm may be electrically connected to the inner conductor of the feedline and furthermore may extend distally from a distal end of the feedline. The helical arm may be coaxially disposed about the linear arm. The linear arm may further include a first portion and a second portion; wherein the first portion is surrounded by a dielectric and the second portion is free of dielectric and is distal relative to the first portion.

The linear arm of the antenna may comprise an extension of the inner conductor of the feedline. The linear arm may be for example, 4 to 14 mm in length. The second portion of the linear arm in some approaches may be longer than the first portion. Where the second portion is longer than the first, the second portion may be of a larger diameter than the inner conductor of the feedline. Alternatively, the first portion of the linear arm may be longer than the second portion. The second portion may be for example 0.1 to 2 mm in length. Where the second portion is longer than the first, the first portion may be 0.1 to 2 mm in length.

The helical arm of the antenna may be 1 to 18 mm in length and or may have 1 to 14 turns.

The helical arm typically does not surround the feedline and/or the outer conductor by more than two complete turns of the helical arm or more than one complete turn. Alternatively, the helical arm may not surround the feedline and/or the outer conductor by more than 2 mm, or by more than 1 mm or by more than 0.5 mm.

Some aspects of the invention may be directed towards the microwave ablation probe further comprising a shaft and wherein the antenna and the feedline are disposed within the shaft. Additionally, the shaft may comprise a metal portion and a ceramic portion. The ceramic portion may extend axially to be at least co-extensive with the antenna.

Aspects of the invention may additionally or alternatively include a cooling system configured to pass a coolant fluid over the antenna. Additionally, the cooling system may be configured to pass a coolant fluid over at least a portion of the feedline and over the antenna and/or comprise a coolant chamber defined between the inner walls of the device shaft. Additionally, the cooling system may comprise a cooling tube disposed about the linear arm.

In additional aspects, the cooling tube may divide the cooling chamber into a first cooling conduit and a second cooling conduit. The first cooling conduit may be disposed between the linear arm and the inner wall of the cooling tube. The second cooling tube may be disposed between the outer wall of the cooling tube and the inner wall of the device shaft. In this arrangement, the linear arm of the antenna may be disposed in the first cooling conduit and the helical arm of the antenna may be disposed in the second cooling conduit.

Additionally or alternatively, the cooling tube may extend over the distal portion of the feedline and extend distally about at least a portion of the antenna.

Additionally or alternatively, the cooling tube is coaxial with the linear arm. Furthermore, the cooling tube may extend to and/or beyond the linear arm of the antenna. In some aspects, the helical arm of the antenna may be wound about the cooling tube and or about the linear arm and extend distally from the junction point in a series of turns about the cooling tube and/or the linear arm, respectively.

In some aspects, the microwave ablation probe may have a metallic cap. Additionally, the linear arm of the antenna may be electromagnetically coupled to the metallic cap but not connected to the cap. Additionally or alternatively, the distal tip of the antenna may be separated from the cap by a distance of 0.2 mm to 3 mm.

An additional aspect of the disclosure is directed towards a microwave ablation needle having a feedline and a shaft. The feedline may be electrically connected to a microwave antenna and the shaft may be surrounding the microwave antenna and the feedline. The shaft may include a non-metallic portion and a metallic portion. The non-metallic portion may extend axially to be co-extensive with at least a portion of the antenna that radiates microwaves.

In some aspects, the non-metallic portion of the shaft may be ceramic. Additionally or alternatively, the microwave ablation needle may comprise a resilient element. The resilient element may be disposed between the non-metallic portion and the metallic portion and may be further configured to provide resilience or strain relief to a joint between the non-metallic portion and the metallic portion of the probe shaft.

In some aspects of the microwave ablation needle described above, the microwave antenna may comprise a helical arm and a linear arm. The helical arm can be electrically connected to the outer conductor of the feedline at a junction point; the helical arm may further be extending in a distal direction from the junction. The linear arm may be electrically connected to the inner conductor of the feedline and furthermore may extend distally from a distal end of the feedline. The helical arm may be coaxially disposed about the linear arm. The linear arm may further include a first portion and a second portion; wherein the first portion is surrounded by a dielectric and the second portion is free of dielectric and is distal relative to the first portion.

Additional aspects of the invention may be directed towards a microwave ablation system having one or more ablation probes; each of the one or more microwave ablation probes may include a feed line, an antenna, a power module, and one or more power cables. The feedline may have an inner conductor, an outer conductor, and a dielectric disposed there-between. The antenna may include a helical arm and a linear arm. The helical arm can be electrically connected to the outer conductor of the feedline at a junction point; the helical arm may further be extending in a distal direction from the junction. The linear arm may be electrically connected to the inner conductor of the feedline and furthermore may extend distally from a distal end of the feedline. The helical arm may be coaxially disposed about the linear arm. The linear arm may further include a first portion and a second portion; wherein the first portion is surrounded by a dielectric and the second portion is free of dielectric and is distal relative to the first portion. The power module may be configured to provide microwave energy to the antenna. The one or more power cables may be configured to connect the power module to each microwave antenna and to deliver microwave energy provided by the power module to the antenna for the ablation of tissue.

Additional aspects of the invention may be directed towards a microwave ablation system for the ablation of tissue having one or more microwave ablation needles, a power module, and one or more power cables. The one or more microwave needles may include a feedline and a shaft. The feedline may be electrically connected to a microwave antenna and the shaft may be surrounding the microwave antenna and the feedline. The shaft may surround the microwave antenna and the feedline and include a non-metallic portion and a metallic portion. The non-metallic portion may extend axially to be co-extensive with at least the radiating portion of the antenna. The power module may be configured to provide microwave energy to the antenna. The one or more power cables may be configured to connect the power module to each microwave antenna and to deliver microwave energy provided by the power module to the antenna for the ablation of tissue.

In some aspects, the microwave ablation system may include a feedline and an antenna. The feedline may have an inner conductor, a dielectric coaxially disposed about the inner conductor, and an outer conductor coaxially disposed about the dielectric. The antenna may include a helical arm and a linear arm. The helical arm may be electrically connected to the outer conductor of the feedline at a junction point and may extend in a distal direction from the junction point. The linear arm may be electrically connected to the inner conductor of the feedline and may extend in a distal direction from a distal end of the feedline. The linear arm may further include a first portion and a second portion. The first portion may be surrounded by a dielectric and the second portion may be free of dielectric and be distal to the first portion.

Additionally or alternatively, the one or more microwave ablation needles may each include a cooling system to cool the antenna and/or at least a portion of the feedline. The ablation system may additionally comprise a cooling system configured to deliver coolant fluid to the cooling systems of the one or more microwave ablation probes, to cool the antenna and at least a portion of the feedline of each of the one or more microwave ablation probes.

In some aspects of the disclosure, the power cables of the one or more microwave ablation needles may be a cooled power cable and the cooling system may be configured to cool the power cables of the one or more microwave ablation needles.

Additionally or alternatively, the majority of the helical arm may not surround the feedline and/or the outer conductor. Furthermore, the outer conductor may not extend distally past the junction point and/or may extend through only a minority of the helical arm. In some aspects of the invention, the helical arm forms no other electrical contacts with the inner conductor or the outer conductor except with the junction point. In one variant of the linear arm, the second portion may be disposed distally to the distal end of the helical arm, such that the second portion does not extend through the helical arm. Furthermore, the helical arm may have a diameter greater than the first portion.

The details of one or more examples set forth in the accompanying drawings and the description below. Other feature, objects, and advantages will be apparent from the description and drawings, and from the claims.

Other embodiments of the invention are discussed throughout this application. Any embodiment discussed with respect to one aspect of the invention applies to other aspects of the invention as well, and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention. The following includes definitions of various terms and phrases used throughout this specification.

The term "spherical shape" means a three dimensional shape that is generally globular.

The term "distal" refers to a position or portion that is furthest from the user and the term "proximal" refers to a position or portion that is closest to the user.

The term "pitch" of a helical antenna is the height of one complete helix turn, measured parallel to the axis of the helix.

The terms "electrically connected," "electrically coupled," or "in electrical contact" is defined as electric current being able to pass from one item to the other. Typically the two items are physically connected by or through a conductor, e.g., a metal wire.

The term "electro-magnetically coupled" is defined as electro-magnetic energy being able pass from one item to the other without a physical contact such as to affect the shape of the energy field and the ablation volume produced. The two items need not be physically connected by or through a conductor, but the electro-magnetic energy can be transferred from one item to the other, e.g., electro-magnetic induction.

The terms "insulating layer," "dielectric," and "insulator," mean a layer of non-conducting material that does not form any electrical contact under operable use of the device. In the embodiments disclosed herein, the insulating layer or dielectric layer are used to prevent undesired electrical contact.

The terms "about" and "approximately" are defined as being close to as understood by one of ordinary skill in the art, and in non-limiting embodiments the terms are defined to be within 20%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The assemblies, devices or methods disclosed herein can "comprise," "consist essentially of," or "consist of" particular method steps, ingredients, components, compositions, etc.

Other objects, features and advantages disclosed herein will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

BRIEF DESCRIPTION OF THE DRAWINGS

Advantages of the present invention may become apparent to those skilled in the art with the benefit of the following detailed description and upon reference to the accompanying drawings.

FIG. 6C is a schematic view of a microwave tissue ablation device with a metal cap according to one embodiment of the invention.

FIG. 6D is a schematic view of a microwave tissue ablation device with a metal cap according to one embodiment of the invention.

Figure 1A:
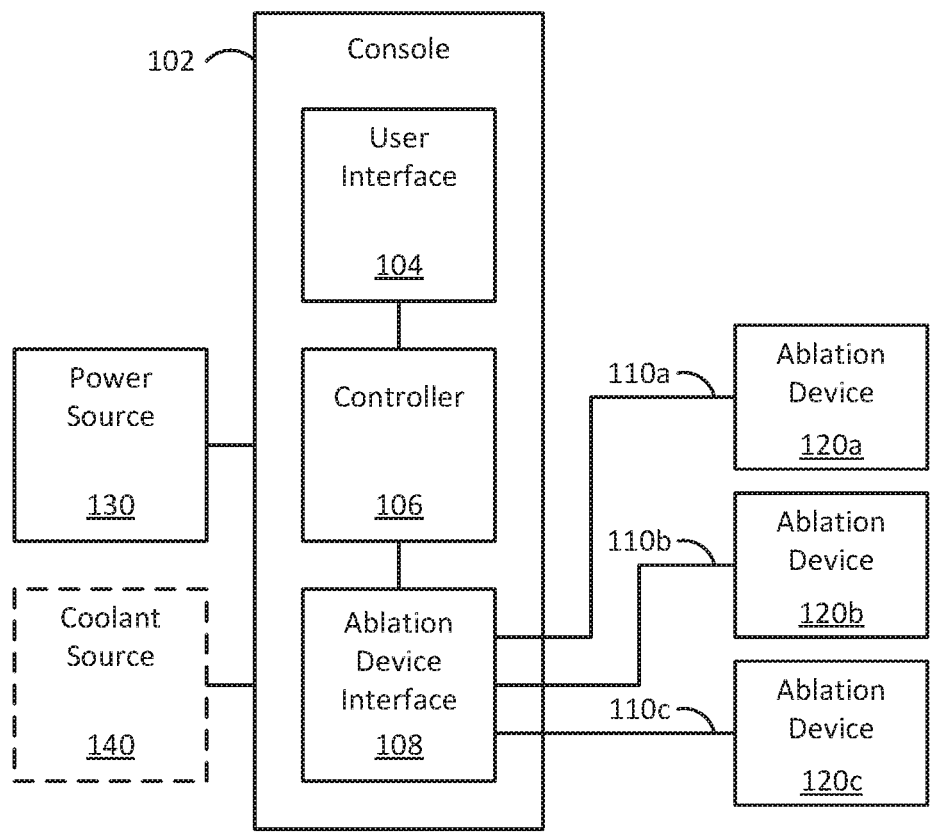
FIG. 1A shows a block diagram including components of a system for performing an ablation process according to an aspect of this disclosure.

While the invention is susceptible to various modifications and alternative forms, specific embodiments thereof are shown by way of example in the drawings. The drawings may not be to scale.

DETAILED DESCRIPTION

The size and dimension of an ablation area created by the microwave tissue ablation device is dependent, among other factors, on the type of microwave antenna. Clinicians may select a microwave antenna capable of generating an ablation region greater than the size and dimension of the target tissue and insert the microwave antenna such that the ablation region created by the microwave antenna includes the target tissue. Where the tissue to be ablated is larger than the size of the ablation volume produced by the device, more than one device may be used and the ablation volumes combined to cover the tissue to be ablated. The embodiments of the microwave tissue ablation device described herein may be used to create predictably shaped ablation regions, with reduced tailing which aids ablation planning and prevents damage to tissue outside the volume to be treated.

In some aspects, the ablation devices disclosed herein are microwave ablation devices; that is to say they cause ablation by emission of microwave energy, which kills the tissue by heating. Typically the devices are microwave ablation needles having microwave antennas such as those described herein. In a further aspect, the invention provides a system for microwave ablation of tissue comprising one or more microwave ablation devices such as probes or needles as described herein, the microwave ablation device comprising a microwave antenna configured to transmit microwave energy to tissue, a microwave generator configured to provide microwave energy to the microwave antenna via a feedline, one or more power cables configured to connect the microwave generator to the microwave antenna of the ablation devices and to deliver microwave energy provided by the microwave generator to the antenna for the ablation of tissue.

Ablation devices such as those described herein can be configured to operate at powers of up to 150 watts and for periods of up to 20 minutes or more. The devices heat up during use due to resistive heating of the antenna and to energy reflected from the tissue and therefore typically at least the distal portion of the device including a distal portion of the feedline and the antenna will require cooling. Conveniently, in various embodiments, the whole feedline and antenna are cooled. Cooling the antenna prevents the device itself becoming damaged and prevents tissue close to the antenna becoming over heated or charred. This alters the physical properties of the tissue, including its energy absorption and reflection characteristics and therefore reduces the efficiency of the antenna and may alter the ablation zone. In an embodiment the tissue ablation devices above therefore may additionally comprise a cooling system to cool the antenna and/or at least a portion of the feed line. Such cooling systems are typically configured to pass a cooling fluid such as a coolant (e.g. water) over at least a portion of the feedline and over the antenna. Typically such systems comprise a coolant inlet and a coolant outlet which co-operate to pass a coolant over the antenna and optionally at least a portion of the feedline to cool the antenna and optionally at least a portion, and may be all, of the feedline. The antenna and feedline are typically in contact with the coolant.

FIG. 1A shows a block diagram including components of a system for performing an ablation process according to one embodiment of the disclosure. The system includes a console 102 including a user interface 104, controller 106, and an ablation device interface 108. In an embodiment, user interface 104 includes a display for presenting information to a user and an input device for receiving inputs from the user, such as via one or more buttons, dials, switches, or other actuatable elements. In an embodiment, user interface 104 comprises a touchscreen display that functions as both the display and the input device of the user interface 104.

According to an aspect of the invention, the ablation device interface 108 of the console 102 is arranged to interface with one or more ablation devices. In the embodiment of FIG. 1A, ablation device interface 108 interfaces with three ablation devices 120a, 120b, 120c via lines 110a, 110b, 110c, respectively. In an embodiment, a console 102 can interface one, two, or all three ablation devices (120a, 120b, 120c) individually or simultaneously. It will be appreciated that, while three ablation devices are shown in the embodiment of FIG. 1A, different aspects of the invention may include a console having an ablation device interface capable of interfacing with different numbers of ablation devices.

In an embodiment, a console includes an ablation device interface capable of interfacing with a single ablation device. In other embodiments, a console includes an ablation device interface capable of interfacing with two ablation devices, with three ablation devices, with four ablation devices, or with five ablation devices. In some examples, an ablation device interface can be configured to interface with any number of ablation devices.

According to certain aspects of the invention, a console can be used to operate any number of ablation devices up to the number of ablation devices supported by the ablation device interface. For example, a console having an ablation device interface capable of receiving three ablation devices simultaneously can be configured to operate one, two, or three ablation devices.

In an embodiment, lines 110a, 110b, 110c are configured to provide a coolant (e.g., from a coolant source 140) and ablation power (e.g., microwave signals) to ablation devices 120a, 120b, 120c, respectively. Lines 110a, 110b, 110c can be configured to provide a path for a coolant to be provided to a respective ablation device and a return path for receiving coolant from the respective ablation device after having traversed a coolant flow path within the ablation device.

According to an aspect of the invention, the controller 106 is configured to interface with the user interface 104 and the ablation device interface 108. In an embodiment, the controller 106 can be configured to receive one or more inputs via the user interface 104 and output one or more items via the user interface 104.

The controller 106 can be configured to control operation of one or more ablation devices (e.g., 120a, 120b, 120c) via the ablation device interface 108. In an embodiment, controller 106 can cause coolant to be provided to one or more ablation devices via the ablation device interface 108. The controller 106 can cause ablation power to be provided to one or more ablation devices in order to cause the ablation device to perform an ablation process. In an embodiment, the ablation power provided to an ablation device causes a microwave ablation device to emit microwave radiation. A power source 130 can provide electrical power used to generate the ablation power.

In an example, the controller includes one or more processors and memory comprising instructions for causing the one or more processors to be performed via the controller. In various embodiments of the invention, a controller may be implemented as one or more processors, such as one or more microprocessors, digital signal processors (DSPs), application specific integrated circuits (ASICs), field programmable gate arrays (FPGAs), programmable logic circuitry, or the like, either alone or in any suitable combination. A controller may also include memory that stores program instructions and related data that, when executed cause the controller to perform the functions attributed thereto in this disclosure. Memory may include any fixed or removable magnetic, optical, or electrical media, such as RAM, ROM, CD-ROM, flash memory, EEPROM, or the like. Memory may also include a removable memory portion that may be used to provide memory updates or increases in memory capacities. A removable memory may also allow image data to be easily transferred to another computing device. A controller may also be implemented as a System on Chip that integrates some or all components of a computer or other electronic system into a single chip.

Figure 1B:
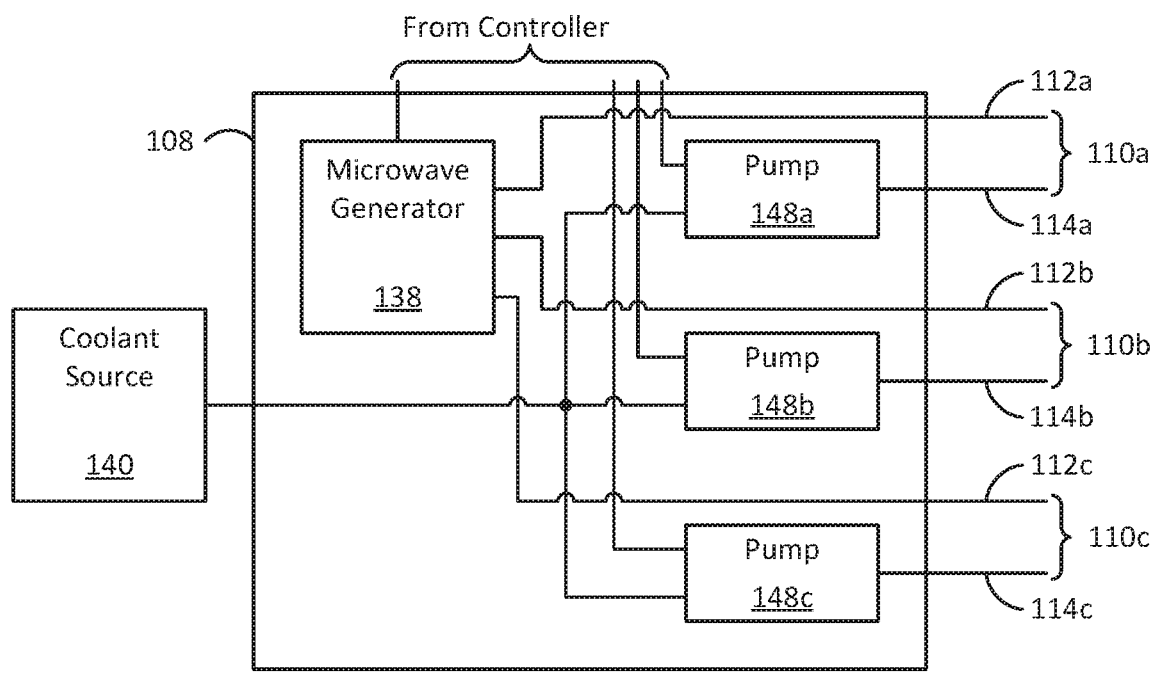
FIG. 1B shows a block diagram demonstrating operation of an ablation device interface for interfacing with an ablation device for performing an ablation process according to an aspect of this disclosure.

FIG. 1B shows a block diagram demonstrating operation of an ablation device interface for interfacing with an ablation device for performing an ablation process according to one embodiment of the disclosure. In an example, an ablation device interface 108 includes one or more fluid pumps, each of the one or more fluid pumps (148a, 148b, 148c) being configured to pump a coolant to a respective ablation device. For example, as shown, pump 148a is in communication with coolant source 140, and can be configured to provide coolant to an ablation device (e.g., 120a) via a coolant line 114a. Such pump(s) can be controlled by the controller. The controller can be configured to control the flow rate of fluid provided from a pump (e.g., 148a) to an ablation device (e.g., 120a), including initiating the pump providing the coolant to the ablation device and stopping the pump providing the coolant to the ablation device.

In the example of FIG. 1B, the ablation device interface 108 includes three pumps 148a, 148b, 148c for providing coolant to a respective ablation device via coolant lines 114a, 114b, 114c, respectively. Coolant lines 114a, 114b, 114c can be included in lines 110a, 110b, 110c shown in FIG. 1, respectively. In an embodiment, each pump is controlled by the controller and independently from the other pumps, for example, whereby any pump can operate independently of the operating status of the other pumps.

In another embodiment, each of pumps 148a, 148b, 148c comprises a peristaltic pump driven by a single motor controlled by the controller. In some such examples, each pump operates at the same rate defined by the motor, and coolant flows through any connected ablation devices via coolant lines 114a, 114b, 114c. The controller can adjust the flow rate of coolant through the ablation devices by controlling the speed of the motor.

In some examples, coolant provided to the ablation device is provided in a closed loop recirculation system, wherein coolant is received from the ablation device and returned to the coolant source 140. In an embodiment, coolant source 140 comprises a reservoir of coolant, such as sterile water, from which coolant is drawn, directed to one or more ablation devices via a coolant line, and returned to the reservoir from the one or more ablation devices via a coolant outlet line configured to carry coolant away from the ablation device. In some alternate examples, coolant outlet line(s) carry coolant away from the ablation device toward to waste (e.g., toward a drain). The ablation device interface of FIG. 1B includes a microwave generator 138 for generating and providing microwave signals to a microwave antenna in a microwave ablation device configured to transmit microwave energy to tissue. Providing microwave signals to the ablation device can include providing ablation power to the ablation device such that the device emits microwave radiation. Microwave generator 138 can provide microwave signals to ablation devices via power cable. In the embodiment of FIG. 1B, microwave generator 138 can provide microwave signals to up to three ablation devices via power cables 112a, 112b, 112c, respectively.

Power cables 112a, 112b, 112c may be coaxial cables which are rated to at least 30 watts, possibly at least 100 watts, and even may be at least 150 watts power. The cables may be cooled cables configured to be cooled by a coolant supply, which may be by circulating coolant along the cable between a cable coolant inlet and a cable coolant outlet. In some examples, fluid lines 114a-c provide coolant along power cables 112a-c, respectively. In an example configuration, the system comprises a cooling system and the cooling system is configured to cool both the cable and the microwave ablation device.

In some examples, the microwave generator may be configured to supply microwave energy to the antenna in one or more of the 915 MHz range the 2.45 GHz range or the 5.8 GHz range. The devices are typically operated in the 2.45 GHz range such as at or about 2.45 GHz. The microwave generator may be configured to provide microwave energy to the antennas of up to 5 microwave ablation probes, and may be of one, two or three probes.

The microwave generator 138 can be configured to provide microwave signals prescribed by the controller 106. For example, in an example embodiment, the controller 106 can instruct the microwave generator 138 to provide particular microwave signals to a particular ablation device. The controller can be configured to designate a particular ablation magnitude (e.g., desired microwave power and/or energy emitted from ablation device, etc.), ablation duration, or other parameters, such as a duty cycle, phase shift, or other parameters associated with the microwave signal. In some examples, the microwave signal includes an electrical power (e.g., 90 W) delivered to the ablation device. The microwave signal can include an electrical signal including properties (e.g., electrical power, frequency, etc.) in order to cause the ablation device to emit microwave radiation having desired characteristics (e.g., microwave power radiated to surrounding tissue, etc.). The electrical signal can provide a desired ablation power to the microwave ablation device.

In an embodiment, the controller 106 can instruct the microwave generator 138 to apply microwave signals to each of a plurality of ablation devices. For example, with respect to FIG. 1B, the controller can instruct the microwave generator 138 to provide a first microwave signal to a first ablation device via power cable 112a, provide a second microwave signal to a second ablation device via power cable 112b, and provide a third microwave signal to a third ablation device via power cable 112c. In some such examples, the microwave generator 138 can provide such first, second, and third microwave signals simultaneously. Such signals can be the same signal or different signals. For example, in an embodiment, the same level of ablation power is provided by each of the first, second, and third microwave signals.

In some examples, the controller may be configured to control one or more of the following parameters: the output wavelength, the output power, the time period over which microwave energy is delivered to one or more of the antennas, the time period over which energy is delivered at an output power. Where the ablation device comprises a sensor, such as a temperature sensor, the controller can be configured to control any one or more of the parameters in response to a signal from the sensor (e.g., a temperature measurement). For example the controller may be configured to switch off the power to one or more of the antennas in response to an over temperature condition.

While shown in FIG. 1B as being implemented as a single microwave generator 138 configured to provide microwave signals to a plurality of ablation devices, in some examples, an ablation device interface 108 can include a plurality of microwave generators, each corresponding to a respective ablation device. In an embodiment, the controller 106 is in communication with a plurality of microwave generators and can be configured to cause the plurality of microwave generators to apply microwave signals to respective power cables (e.g., 112a, 112b, 112c) to provide such microwave signals to respective ablation devices.

FIG. 1B shows an example embodiment wherein three lines 110a, 110b, 110c can provide microwave signals and coolant to a respective three ablation devices simultaneously. In some aspects of the invention, microwave signals and coolant can be provided to a subset of lines 110a, 110b, 110c, for example, if fewer than three ablation devices are connected to the console 102. Further, in some aspects, microwave signals and coolant can be provided to a subset of lines 110a, 110b, 110c even if three ablation devices are connected to the console 102. For example, one or more such connected ablation devices can remain unused.

In an embodiment, controller 106 controls which ablation devices (e.g., which lines of 110a, 110b, 110c) receive microwave signals and coolant. In an aspect of the invention, the controller 106 can control aspects of the microwave signal, such as magnitude, frequency, duty cycle, duration, etc. of the microwave signal. In another aspect of the invention, the controller 106 can control aspects of providing the coolant to an ablation device, such as controlling a flow rate of the coolant, for example, by controlling operation of a respective pump. In an embodiment, for each ablation device, the controller controls aspects of both the microwave signal applied to an ablation device and aspects of providing the coolant to the ablation device. During operation, different ablation devices can each receive microwave signals and amounts of coolant independent of the signals and fluid received at other ablation devices, and can be the same as or different from microwave signals and amounts of fluid provided to other ablation devices.

While FIG. 1B shows an ablation device interface for interfacing with three ablation devices, it will be appreciated that a console according to different embodiments can include an ablation device interface capable of interfacing with a different number of ablation devices.

It will be appreciated that, while the block diagram of FIG. 1B shows an ablation device interface 108 including several components for interfacing with ablation devices, the components shown as being a part of the ablation device interface 108 are not necessarily contained within a single module or housing. Such components are grouped into the ablation device interface in that such components facilitate control of connected ablation devices by controller 106.

Additionally, while FIG. 1B shows an ablation device interface for interfacing with microwave ablation devices, it will be appreciated that similar ablation device interface concepts can be used to provide an interface between a controller and other ablation devices, such as RF ablation, cryoablation, or the like.

In an embodiment, the ablation device interface includes one or more ports configured to receive a portion of an ablation device, such as a cartridge having a fluid interface for connecting to a fluid line (e.g., 114a) and an electrical interface for connecting to a power cable (e.g., 112a).

Figure 2:
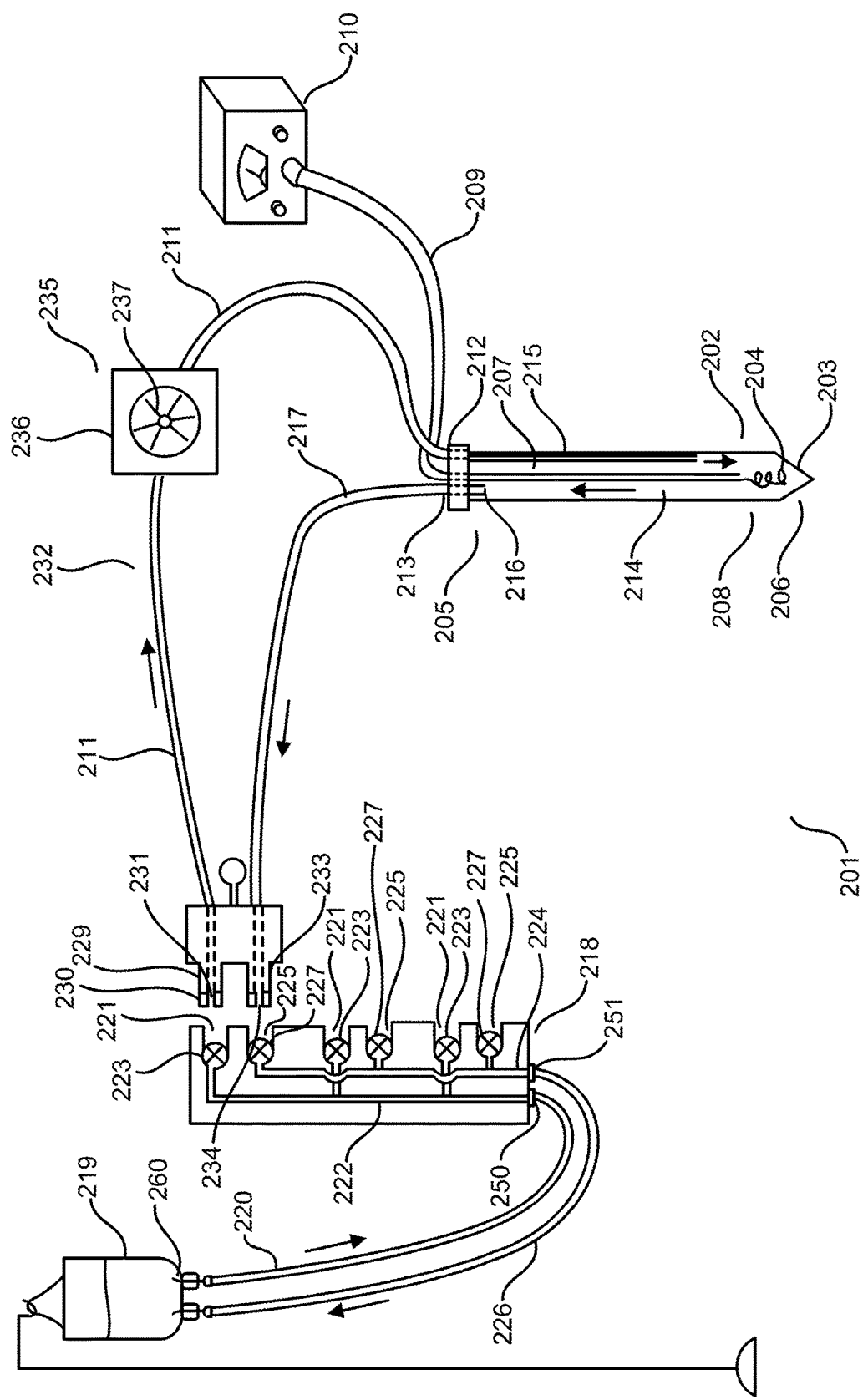
FIG. 2 is a simplified illustration of a cooling system according to an aspect of this disclosure.

FIG. 2 is a simplified illustration of a cooling system according to the disclosure. The system 201 comprises an ablation device 202. In this case the microwave ablation device comprises a microwave ablation needle which is configured to deliver microwave energy to a patient's tissue to ablate the tissue.

The microwave ablation device 202 may have a tip 203 configured to penetrate tissue and an elongated shaft having a proximal end 205 and a distal end 206. The shaft encloses a coolant space 214 and a feedline 207, which may be a coaxial cable having an inner conductor, an outer conductor, and a dielectric there between (not shown in FIG. 2). The feedline of FIG. 2 comprises, distally, a radiating region 208 comprising a microwave antenna 204. The proximal end of the feedline 207 may be attached to a cable 209 (typically a coaxial cable) connecting the microwave ablation device 202 to a microwave generator 210 for providing microwave energy to the device. The cable may be reasonable connectable, or, as in this case, permanently attached to the device. In some embodiments, as shown with respect to FIG. 1, the microwave generator 210 may be housed within a console, such as console 102.

The device is provided with coolant via a device coolant supply line 211 which may be permanently attached to the device coolant inlet 212. In some embodiments, the device coolant supply line may, alternatively, be releasably connectable to the coolant inlet 212 such as via a Luer® type connector. The device coolant inlet 212 is in fluid communication with the device coolant outlet 213, via a series of coolant passageways 214, 215, and 216 configured to circulate coolant within the device. In this simplified representation, coolant enters the device through the coolant inlet tube 215, circulates through a coolant chamber 214 to cool the device, and leaves via the coolant outlet tube 216 and device coolant return line 217.

System 201 is provided with a manifold 218 which receives coolant fluid from a coolant fluid source 219, via a coolant system supply line 220. The coolant system supply line 220 may be permanently connected to the manifold 218 at the manifold fluid supply inlet 250 or it may be releasably connectable to the supply inlet 250, for example by a LuerLok® connector. The coolant fluid source may be, for example, an IV bag. The in-flowing coolant may be distributed to one or more manifold outlet ports 21, via a manifold inflow conduit 222. In an advantageous embodiment, and as illustrated in FIG. 2, flow of coolant out of the port 221 may be controlled by a manifold outlet valve 223. This valve may be normally in the closed position. In some embodiments, as shown with respect to FIG. 1, the manifold 218 may be housed within a console, such as console 102.

The manifold 218 also comprises a manifold coolant outflow conduit 224 which provides a fluid connection between one or more manifold fluid inlet ports 225 and the coolant system return line 226. The coolant system return line 226 may be permanently connected to the manifold 218 at the manifold fluid return inlet 251 or it may be releasably connectable to the supply inlet 250, for example by a LuerLok® connector. In an aspect of the design, a manifold inlet valve 227 controls the flow through each inlet port and may also normally be in the closed state.

A supply coupling 229 is configured for connection to a manifold outlet port 221. The system may also comprise a return coupling 233 which is configured for connection to a manifold inlet port. In one aspect, the manifold outlet valve 223 may be configured to open upon connection of the supply coupling 229. In one approach, the supply coupling may comprise projections 230 which cause the valve to open upon connection of the coupling 229, to the port 221, but other arrangements are possible as discussed elsewhere herein.

A coolant circuit coolant inlet 231 on the supply coupling 229 is in fluid communication with the device coolant supply line 211 so that connection of the supply coupling 229 to the outlet port 221 places the cooling circuit 232 in fluid communication with the cooling fluid supply 219.

A return coupling 233 may have a coolant circuit outlet 234 in fluid communication with the device coolant return line 217. The supply coupling 229 and the return coupling 233 can be arranged for simultaneous connection to the manifold outlet port 221 and inlet port 225 respectively.

A pumping portion 235 may be arranged in the device cooling circuit 232 and may be arranged in the supply line 211 for example, and is arranged to circulate the coolant through the microwave ablation device 202. In the system shown in FIG. 2, the pump is a disposable pump head 236 having pump vanes 237, permanently connected in the device coolant supply line and adapted to be connected to a pump head drive (not shown). Alternative pumping portions may be used and are described elsewhere herein. In some embodiments, as shown with respect to FIG. 1A or 1B, the pumping portion 235 may be housed within a console, such as console 102.

Figure 3A:
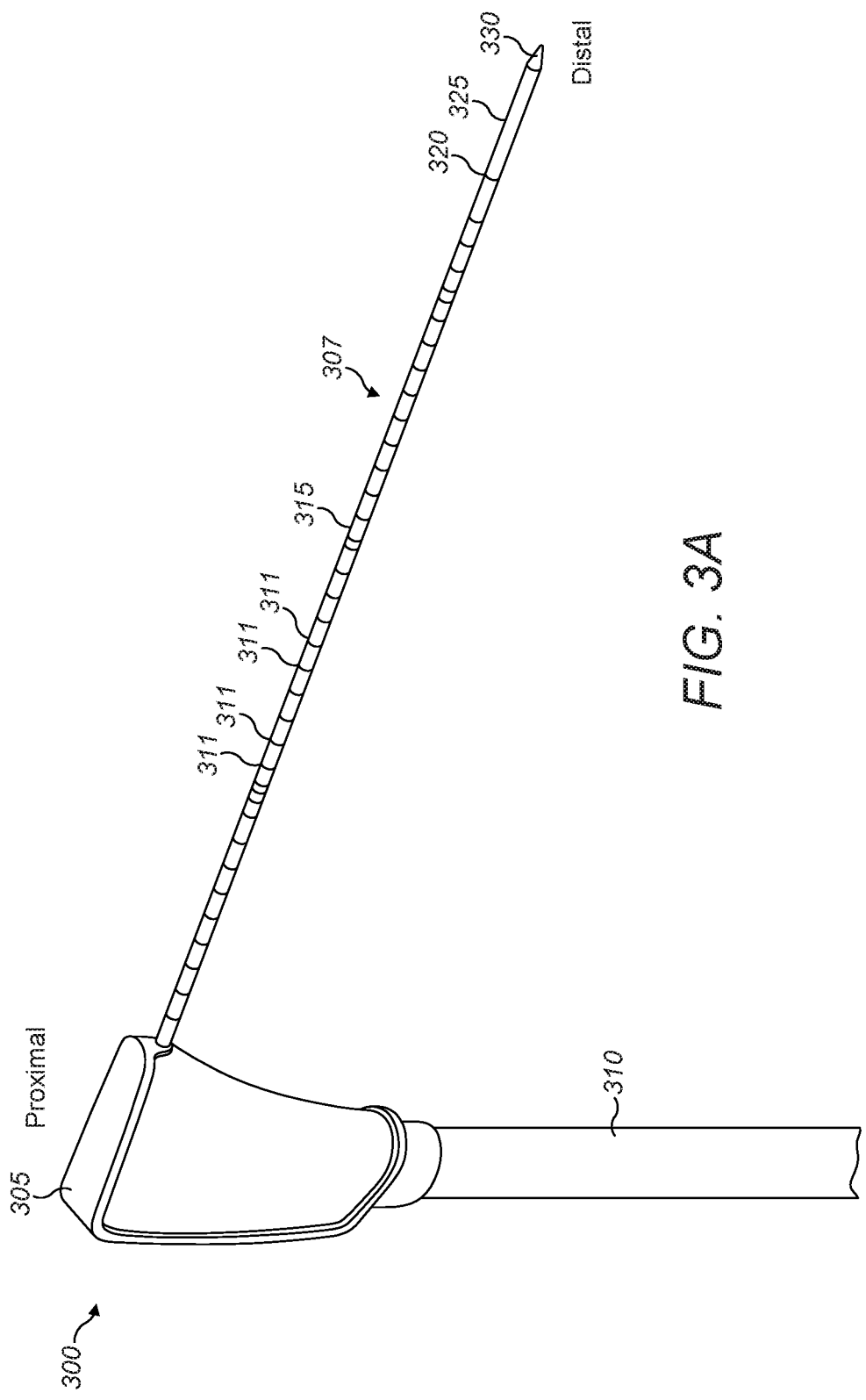
FIG. 3A is a perspective view of a microwave tissue ablation device with its handle according to one embodiment of the disclosure.

FIG. 3A is a perspective view of a microwave tissue ablation device 300 with a handle 305 according to one embodiment of the disclosure.

The microwave tissue ablation device 300 includes a handle 305. The handle 305 is configured to provide a firmer grip for a surgeon to handle the tissue ablation device 300. The handle is further configured to house liquid manifolds for coolant circulation and coaxial connectors for powering the feedline.

The microwave tissue ablation device 300 includes a probe 307. The probe 307 is configured to be inserted into patient's body for heating target tissue. In one embodiment, the probe 307 includes various ablation device components described elsewhere herein, such as the feedline, asymmetric dipole antenna, cooling system having inflow tubes and outflow tubes, etc. In an embodiment, the microwave antenna is configured to emit microwave radiation in a frequency band selected from the 915 MHz band (902 to 928 MHz) the 2.45 GHz band (2.402 to 2.483 GHz) and/or the 5.8 GHz band (5.725 to 5.875 GHz). The wavelength may be within the 2.45 GHz band and particularly the antenna may be configured to emit microwave energy at or about 2.45 GHz. The devices are configured to operate at up to 150 watts power supplied to the antenna.

The probe 307 includes a surface 315. The surface 315 is configured to be in contact with human tissue and is made with biocompatible materials. The device shaft is at least partially, metal, e.g., stainless steel and includes markings 311, e.g., laser markings. The markings 311 are configured to inform the surgeon of the depth of the probe penetration into the body. It may comprise a lubricious surface layer such as PTFE, to aid insertion and prevent tissue sticking to it.

The shaft of devices herein is typically cylindrical and is typically made of a biocompatible polymer, a biocompatible composite material, such as glass fiber reinforced polymer or carbon fiber reinforced polymer, ceramic or metal (such as stainless steel). The shaft may be made of ceramic or metal, but in an optional embodiment the shaft comprises metallic portion and a non-metallic portion. The non-metallic portion may be a biocompatible composite material, such as glass fiber reinforced polymer or carbon fiber reinforced polymer or ceramic, but may be ceramic due to its improved performance and strength. The ceramic may be an alumina or zirconia ceramic.

The shaft of the devices optionally terminates distally in a device cap. The shaft may be cylindrical. The feedline and antenna are optionally disposed within the device shaft. The device shaft typically extends from a proximal manifold and terminates distally in a distal cap. The manifold comprises electrical connections to electrical components of the shaft such as the feedline, and may also comprise coolant inlet and outlet connections, where necessary.

The diameter of the shaft is not limited, and is typically adapted for the intended purpose, for example for ablation needles, it is important to have a narrow needle to limit damage caused at insertion and to provide fine control of positioning, consequently the needle shaft is between 1.4 and 3 mm in diameter, optionally between 1.5 and 2.5 mm, particularly 2 to 2.5 mm.

The devices herein as illustrated by probe 307 of FIG. 3A may include an applicator cap 330. In an embodiment, applicator cap 330 is made of a biocompatible metal or a ceramic, e.g., optionally stainless steel or a ceramic. The applicator cap 330 can include a circular base and a distal tip (e.g., a trocar tip). The applicator cap 330 tip can include a sharp end disposed at a distal end of the applicator cap 330 and configured for penetration of tissue. The circular base can be configured to be sealed with a sheath of the probe 307 such that the interior of the probe 307 is fluidly isolated from the exterior of the probe 307.

The shaft of devices herein may further comprise an echogenic region on the outer surface configured to be visible under ultrasound, imaging. In one embodiment, this region comprises a coating comprising acoustically-reflective microspheres. The echogenic region extends at least to cover the region of the shaft radially outward of the antenna. The probe 307 of FIG. 3A includes an echogenic region 325 configured to be visible under ultrasound, imaging and one embodiment, comprises a coating comprising acoustically-reflective microspheres Where the shaft of devices of the invention comprise a metallic portion and a non-metallic portion, the joint between the two portions, where the metallic portion and the non-metallic portion abut, may be a point of potential weakness, especially where the non-metallic portion is ceramic, since ceramic is typically less flexible and more brittle than metals such as stainless steel. The shaft may therefore additionally comprise a resilient element between this portion and the metallic portion configured to provide resilience to the joint between the non-metallic (e.g., ceramic) portion and the metallic portion of the probe shaft in use.

The devices, (with reference to probe 307) may include a region 320 configured to relieve strain on the probe induced during use, such as that caused by flexing of the shaft. This region may include a resilient element positioned between the metallic and non-metallic portions of the shaft. This strain relief region is particularly useful when the distal portion of the probe sheath is ceramic. The strain relief region 320 is configured to provide the probe 307 added resilience to the joint.

Although a resilient element may also be present between a non-metallic region and the cap, it is not necessary since the strains on the shaft at this point are lower. The strain relief region may, for example, comprise a resilient annular spacer, which may be made of a resilient thermoplastic elastomer, such as polyether block amide (PEBA)—tradename PEBAX® or Vestimid®E (Evonik Industries) or a polyaryletherketone (PAEK) such as Polyether ether ketone (PEEK). The spacer may be shaped and configured to space apart the proximal end of the non-metallic portion from the distal end of the metallic portion. The resilient spacer optionally abuts the metallic portion on a proximal face and the non-metallic portion on a distal face. The resilient annular spacer typically extends radially outward to form a surface flush with the outer surface of the probe shaft. The radially inner portion of the annular spacer may be extended proximally and/or distally to provide an annular step configured to support the inner face of the he proximal end of the non-metallic portion and/or the distal end of the metallic portion. In one optional embodiment, the annular spacer is extended proximally to provide an annular step configured to support the inner face of the distal end of the metallic portion, but does not extend distally. The device shafts may also comprise an adaptor sleeve to support the joint between the non-metallic portion and the metallic portion of the shaft. The adaptor may be configured to take account of any differences in thickness between the non-metallic portion and metallic portion of the shaft, such as to provide a smooth surface transition between the metallic and non-metallic portions. It may be metallic, or non-metallic such as a thermoplastic elastomer, such as a PEBA PEBAX® or Vestimid®E or a PAEK such as PEEK. The adaptor is particularly important where the non-metallic portion is ceramic due to the thickness required for additional strength of the ceramic and the danger of flexing of the shaft causing cracking at this point. Conveniently the sleeve extends each side of the joint sufficiently to provide support for the joint and is typically positioned radially inward of the shaft, typically between the feedline and the inner wall of the shaft. The adapter sleeve may be metallic.

The resilient spacer and the adaptor sleeve (where present) together comprise a strain relief region. The resilient spacer and the adaptor sleeve may be a single piece or separate, where they are a single piece it may be non-metallic and optionally of a thermoplastic elastomer as described above.

In one optional embodiment, the strain relief region comprises a resilient spacer as described above, shaped and configured to space apart the proximal end of the non-metallic portion from the distal end of the metallic portion, the spacer configured to abut the metallic portion on a proximal face and the non-metallic portion on a distal face, the spacer extending radially outward to form a surface flush with the outer surface of the probe shaft, the radially innermost portion of the spacer extending proximally to provide an annular step configured to support the inner face of the distal end of the metallic portion of the shaft; the strain relief region additionally comprising an adaptor sleeve, which may be metallic, extending each side of the joint and radially inward of the annular spacer. Optionally the sleeve extends proximally of the annular spacer and is configured to be in contact with and support the inner face of the distal end of the metallic portion of the shaft; and optionally extends distally of the spacer and is configured to be in contact with and support the inner face of the proximal end of the ceramic portion of the shaft.

The microwave tissue ablation device illustrated 300 includes a housing 310. The housing 310 houses coaxial cables, fluid lines, electric lines, etc.

Figure 3B:
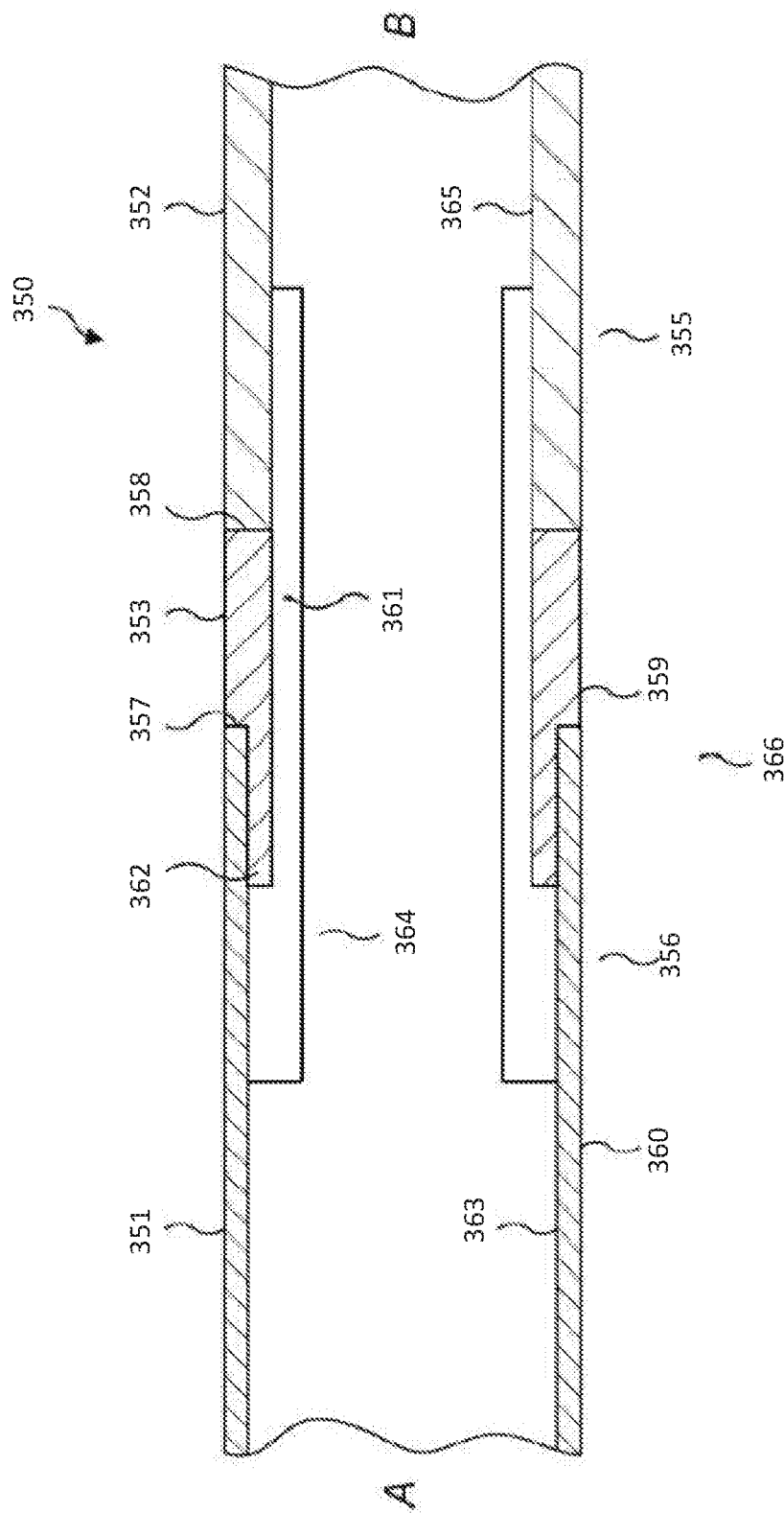
FIG. 3B is an enlarged view of a section of an ablation device shaft showing a joint between a metallic portion and a ceramic portion of the shaft.

FIG. 3B shows a section through one embodiment of a shaft 350 of the device and illustrates a strain relief region 366. The proximal end of the shaft is indicated by A and the distal end by B. Other features such as the coaxial cable, antenna and cooling system are omitted for clarity. The shaft has a proximal metallic portion 351, and a distal non-metallic portion, which may be made of ceramic 352. The shaft comprises a strain relief region 366, comprising a resilient element in the form of a resilient annular spacer 353, positioned between the metallic and non-metallic portions of the shaft, and optionally an adapter sleeve 364, radially inward of the resilient spacer 353.

The resilient annular spacer 353 may be shaped and configured to space apart the proximal end of the non-metallic portion 355 from the distal end of the metallic portion 356. The spacer is configured to abut the metallic portion on a proximal face 357 and the non-metallic portion on a distal face 358. The spacer extends radially outward to form a surface 359, which is flush with the outer surface of the probe shaft 360. The radially innermost portion of the annular spacer 361 may extend proximally to provide an annular step 362, configured to support the inner face of the distal end of the metallic portion 363. An adaptor sleeve 364 may be positioned to extend each side of the joint between the metallic and non-metallic sections and radially inward of the annular spacer 353. Optionally the sleeve extends proximally of the annular spacer 353, and is configured to be in contact with and support the inner face of the distal end of the metallic portion 363 of the shaft 360. The sleeve extends distally of the spacer 353, and is configured to be in contact with and support the inner face of the proximal end of the ceramic portion of the shaft 365. The resilient annular spacer and the optional sleeve form a strain relief region.

Figure 4:
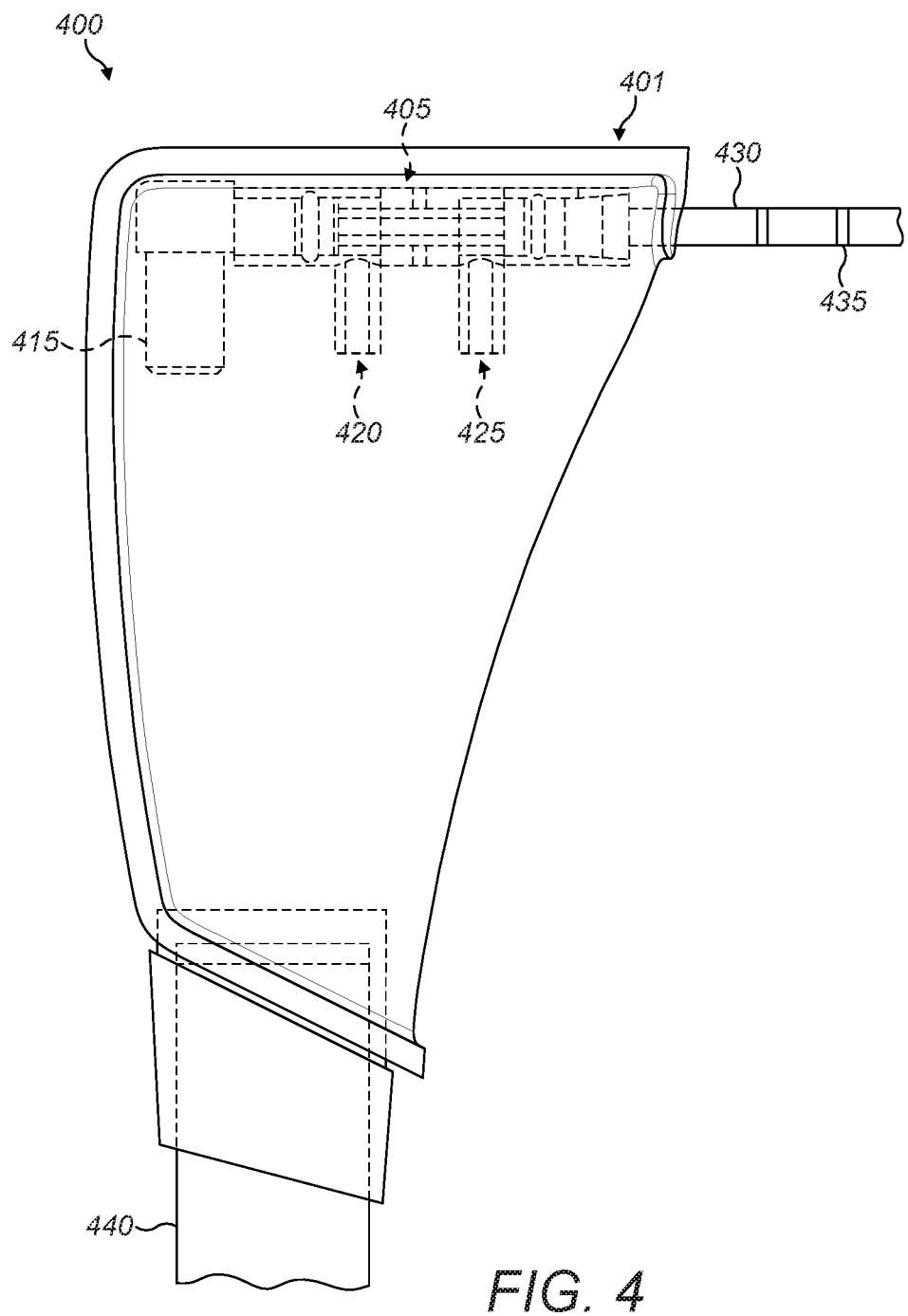
FIG. 4 is a side view of the handle of the microwave tissue ablation device according to one embodiment of the disclosure.

FIG. 4 is a side view of a microwave tissue ablation device 400 of an aspect of the design. The ablation device 400 includes a handle 401. The handle 401 houses a manifold 405.

The manifold 405 electrically connects the power source (not shown) and the tissue ablation probe 430 through the coaxial cable connector 415. The tissue ablation probe 430 includes markings 435 configured to inform surgeons of the depth of probe penetration during surgery.

The manifold 405 also fluidically connects the coolant source (not shown) and the tissue ablation probe 430. The manifold 405 includes a coolant inlet 420 and a coolant outlet 425. The coolant inlet 420 is fluidically connected to the coolant inflow conduit and the coolant outlet 425 is fluidically connected to the coolant outflow conduit.

The tissue ablation device 400 further includes tubular housing 440 that houses the electric wires and fluid tubes. As discussed elsewhere herein, a plurality of ablation devices can be used simultaneously to perform ablation processes. Such ablation devices may be arranged in a variety of ways. In an example, microwave ablation devices can be positioned equidistant form each other. Positioning the ablation devices equidistant from one another may advantageously provide an approximately symmetric net ablation volume formed by the plurality of ablation devices. Additionally, arranging the ablation devices in a regular polygon formation may provide an approximately spherical net ablation volume formed by the plurality of ablation devices. Alternatively, other arrangements, a plurality of devices arranged in a line, or in an irregular shape. Ablation devices can be arranged in a plurality of configurations to provide a desired ablation volume appropriate for a particular operation. In addition, such devices can be inserted to the same or different penetration depths. Similar to different plan arrangements, ablation devices can be arranged in a plurality of configurations to provide a desired ablation volume appropriate for a particular operation.

In one option the cooling system comprises a coolant chamber surrounding the antenna and at least a distal portion of the feedline and having a coolant inlet conduit, configured to supply coolant to the coolant chamber and a coolant outlet conduit configured to carry coolant away from the coolant chamber, the coolant inlet and coolant outlet conduits configured to pass coolant over at least a portion of the feedline and at least a portion of the antenna.

Figure 5:
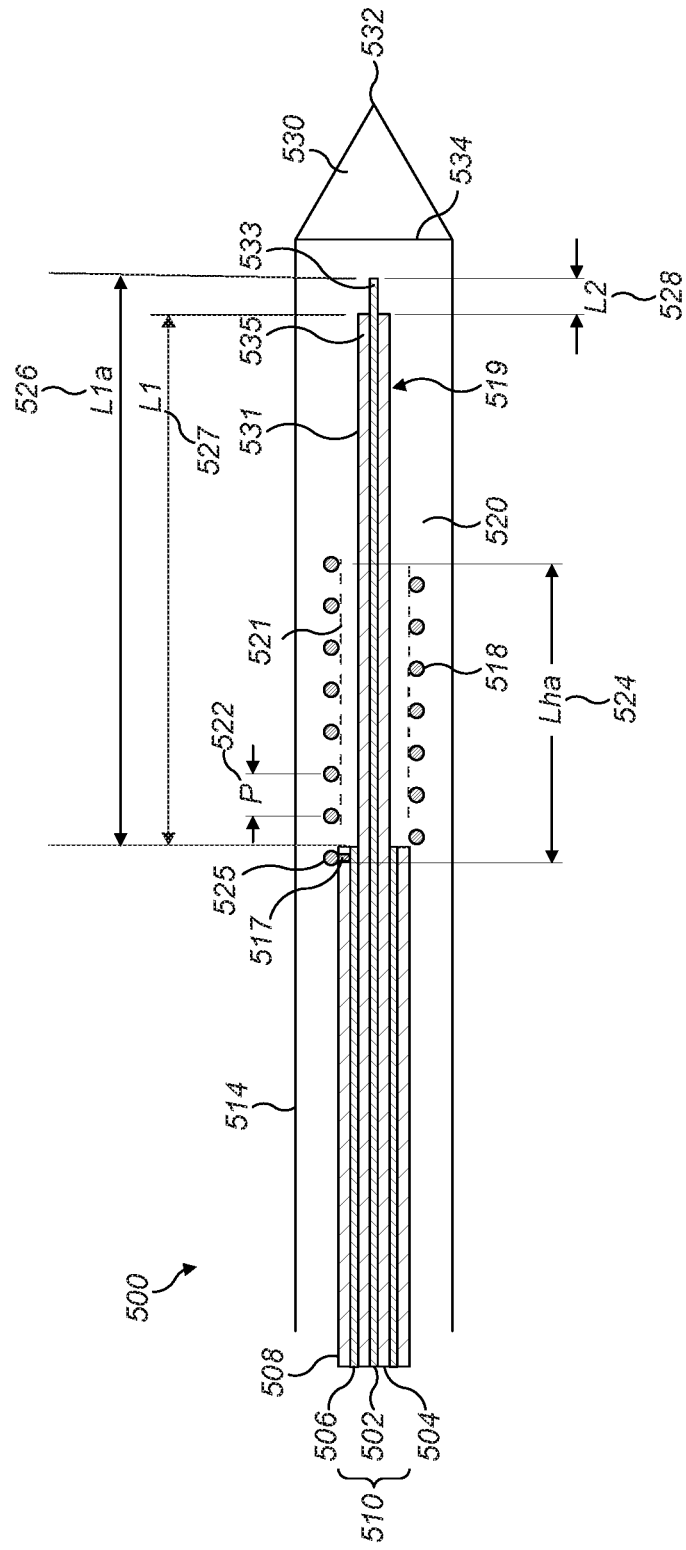
FIG. 5 is a simplified sectional view of a microwave tissue ablation device according to one embodiment of the disclosure.

FIG. 5 is a schematic side view of the distal end of a microwave tissue ablation device 500. The device has been simplified for ease of illustration. FIG. 5 is generally illustrative of the features of the asymmetric antenna.

As shown in FIG. 5, the ablation device 500 includes a coaxial feedline 510. The feedline 510 may include an inner conductor 502. The feedline 510 includes a first insulator 504 disposed concentrically and circumferentially about the inner conductor 502. The inner conductor 502 may be the power line. The feedline 510 includes an outer conductor 506 disposed concentrically about the first insulator 504. The outer conductor 506 may be the ground line. The feedline 510 includes a second insulator 508 disposed concentrically about the outer conductor 506.

The ablation device 500 includes an asymmetric dipole antenna 520. The asymmetric dipole antenna 520 includes a helical arm 518. The proximal end 525 of the helical arm 518 forms an electrical connection with the outer conductor 506 of the feedline 510 at a junction point 517. The junction point may be disposed at or near to the distal end of the feedline. The helical arm 518 extends distally from the junction point 517 in a series of turns. The helical arm 518 forms no other electrical contact with the inner conductor 502 or the outer conductor 506, except the junction point 517.

In the antennas disclosed herein, and with reference to FIG. 5, the helical arms of the antennas 518 have a length Lha 524. For each complete helical turn, the height measured axially is a pitch, P 522. The number of helical turns and pitch (P) can affect the output of microwave energy, the shape of the emission field, and the energy absorption spectrum.

The asymmetric dipole antennas 520 further include a linear arm 519. The linear arm 519 is electrically connected to the inner conductor 502 of the feedline 510, and may, for example, comprise a continuation of the inner conductor. The linear arm 519 extends distally from a distal end of the inner conductor 502. The helical arm 518 extends distally from the junction point 517 in a series of turns about the linear arm 519, such that the linear arm 519 extends through the helical arm 518. A portion of the linear arm may be disposed distally of the distal end of the helical arm. The helical arm 518 may be coaxial with the linear arm 519, which itself may be co axial with the shaft of the device 514. The linear arm 519 may extend through the majority of the helical arm 518, distal to the junction 517 at the proximal end 525 of the helical arm 518. Accordingly, the majority of the helical arm 518 does not surround the outer conductor 506 or the second insulator 508. The outer conductor 506 and any second insulator present 508 may not extend past or much past the junction 517 at the proximal end 525 of the helical arm 518. The outer conductor 506 and any second insulator 508 may extend only through a minority of the helical arm 518. Typically the distance between the junction point and the distal end of the feedline is not more than that required to place and support the connection between the outer conductor and the proximal end of the helical arm. Typically this is no more than two complete turns of the helical arm and optionally less than one complete turn. Typically the distance between the junction point and the distal end of the feedline is 2 mm or less, particularly 1 mm or less and optionally 0.5 mm or less.

The linear arm 519 further includes a first portion 531 surrounded by a dielectric 535. This dielectric 535 can be an extension of the first insulator 504 disposed between the inner 502 and outer 506 conductor of the feedline 510. The linear arm 519 further includes a second portion 533 lacking dielectric. The second portion 533 is distal to the first portion 531.

In one approach the second portion of the linear arm may be shorter than the first portion, as illustrated here. Alternatively, the second portion may be longer than the first portion, as illustrated in FIG. 5D.

In one approach, the helical arm 518 may be located proximally to the second portion, such that the helical arm extends about the first portion 531 but not the second portion. This is particularly the case where the first portion 531 is longer than the second portion 533, as illustrated in FIG. 5. An alternative approach is illustrated in FIG. 5D.

The helical arm 518 may extend about the first portion 531 but may have a diameter greater than the first portion 531, thereby creating a separation distance therebetween, such that the helical arm is disposed radially outward of the linear arm, but radially inward of the inner wall of the shaft. The helical arm 518 may be self-supporting, or it may be supported on its inner surface or its outer surface. In FIG. 5, the helical arm is physically supported on its inner surface via a support substrate 521, but it may be supported in other ways, for example, it may be supported on a cooling tube as illustrated in FIGS. 5C and 5D.

The linear arm 519 has a length L1a 526. The first portion 531 of the linear arm 519 has a length L1 526. The second portion 533 of the linear arm 519 has a length L2 528.

In the illustration of FIG. 5, the linear arm does not contact the base 534 of the applicator cap 530. See FIG. 6 for alternative arrangements.

The antenna and feed line may be contained within a shaft 514 having a separate distal applicator cap 530, attached and sealed to the shaft 514. The applicator cap 530 is made of a biocompatible metal or a ceramic, e.g., optionally stainless steel or a ceramic. The portion of the applicator cap 530 distal to the circular base 534 is in a cone shape. The applicator cap 530 includes a sharp end 532 disposed at a distal end of the applicator cap 530 and configured for penetration of tissue. The applicator cap 530 includes a circular base 534 configured to be sealed with the sheath 514.

The ablation device 500 may comprise a cooling system configured to cool the antenna and/or the feed line. FIG. 5A to FIG. 5D provide further illustrative embodiments of the device, incorporating cooling systems. The features of the antenna illustrated in FIGS. 5A to 5D may be combined with any of the cooling systems illustrated in those figures. For the avoidance of doubt, ribbon and wire type helical arms may be used in each cooling system and the variations in the length and configuration of the linear arm may also be used in any of the cooling systems shown.

Figure 5A:
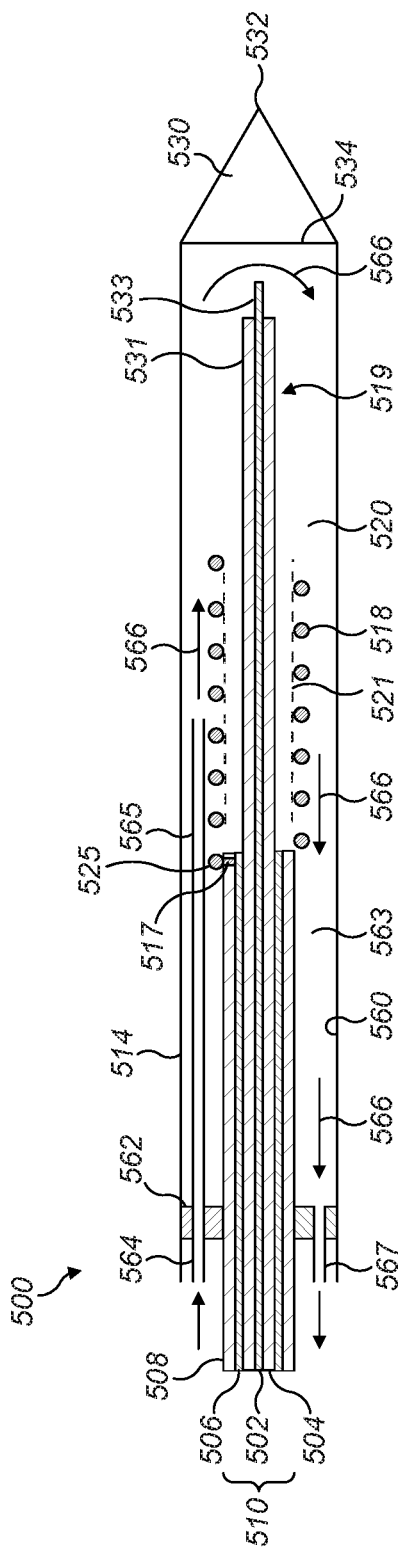
FIG. 5A is a simplified sectional view of a microwave tissue ablation device having a cooling system according to one embodiment of the disclosure.

FIG. 5A illustrates an embodiment of a device of the invention having a cooling system. Other features of the device in FIG. 5A are illustrative.

As per the device illustrated in FIG. 5, the device illustrated in FIG. 5A 500, includes a coaxial feedline 510 including an inner conductor 502, a first insulator 504 disposed concentrically about the inner conductor 502, an outer conductor 506 disposed concentrically about the first insulator 504 and a second insulator 508 disposed concentrically about the outer conductor 506.

The ablation device 500 also includes an antenna 520 having a helical arm 518, the proximal end 525 of which forms an electrical connection with the outer conductor 506 of the feedline 510 at a junction point 517 towards the distal-most end of the feedline. The helical arm 518 extends distally from the junction point 517 in a series of turns. The antenna 520 also includes a linear arm 519. The linear arm 519 is electrically connected to the inner conductor 502 of the feedline 510. The linear arm 519 extends distally from a distal end of the inner conductor 502 and includes a first portion 531 surrounded by a dielectric 535, and a second portion 533 lacking dielectric. As in FIG. 5, the helical arm 518 extends distally from the junction point 517 in a series of turns about the linear arm 519, such that the linear arm 519 extends through the helical arm 518. The helical arm 518 may be coaxial with the linear arm 519. The linear arm 519 may extend through the majority of the helical arm 518, distal to the junction 517 at the proximal end 525 of the helical arm 518. Accordingly, the majority of the helical arm 518 does not surround the outer conductor 506 or the second insulator 508. The outer conductor 506 and the second insulator 508 may not extend past or much past the junction 517 at the proximal end 525 of the helical arm 518. The outer conductor 506 and the second insulator 508 may extend only through a minority of the helical arm 518. The helical arm 518 is located proximally to the second portion, such that the helical arm extends about the first portion 531, but not the second portion of the linear arm. The helical arm 518 may extend about the first portion 531 but may have a diameter greater than the first portion 531, thereby creating a separation distance therebetween as discussed elsewhere herein. The helical arm 518 may be self-supporting, or it may be supported on its inner surface or its outer surface. In FIG. 5A, the helical arm is physically supported on its inner surface via a support substrate 521. The helical arm 518 forms no other electrical contact with the inner conductor 502 or the outer conductor 506, except the junction point 517. As in FIG. 5 the linear arm does not touch the applicator cap 530.

The antenna and feed line are contained within a shaft (shown simplified in this FIG. 514 terminating distally in a separate metallic applicator cap 530 having a sharp end 532 disposed at its distal end as per the device of FIG. 5.

FIG. 5A is illustrative of general features of one type of cooling arrangement, applicable to arrangements of antennas described herein.

A coolant chamber 563 may be defined between the inner walls 560 of the shaft 514. The cooling chamber 563 may be bounded distally by the base 534 of the cap 530 and may be bounded proximally by a seal 562 or other stopper positioned at a point distal of the manifold (not shown) and the antenna 520, through which the feedline 510 passes. A coolant inlet conduit 564 and a coolant outlet conduit 567 also pass through the seal or stopper 562. The coolant inlet conduit 564 may be in the form of a coolant inlet tube 565 disposed within the coolant chamber 563 and displaced radially outward of the feedline 510. The coolant inlet tube 565 may be sized and configured to pass between the antenna 520 and the inner wall 560 of the shaft and to deliver coolant from a coolant outlet of the coolant tube 565 to a position adjacent a portion of the antenna 520.

The coolant inlet conduit 564 may terminate close to the seal 562 or may be extended so as to deliver cooling fluid to any part of the chamber. Delivery close to the antenna 520 is advantageous because it ensures fresh cooling fluid passes over the antenna. A coolant outlet tube 567, or return tube may receive coolant flowing out of the coolant chamber 563. By passing cooling fluid through the cooling chamber in this way, at least a portion of the heat generated in the antenna and/or the feedline can be dissipated.

Figure 5B:
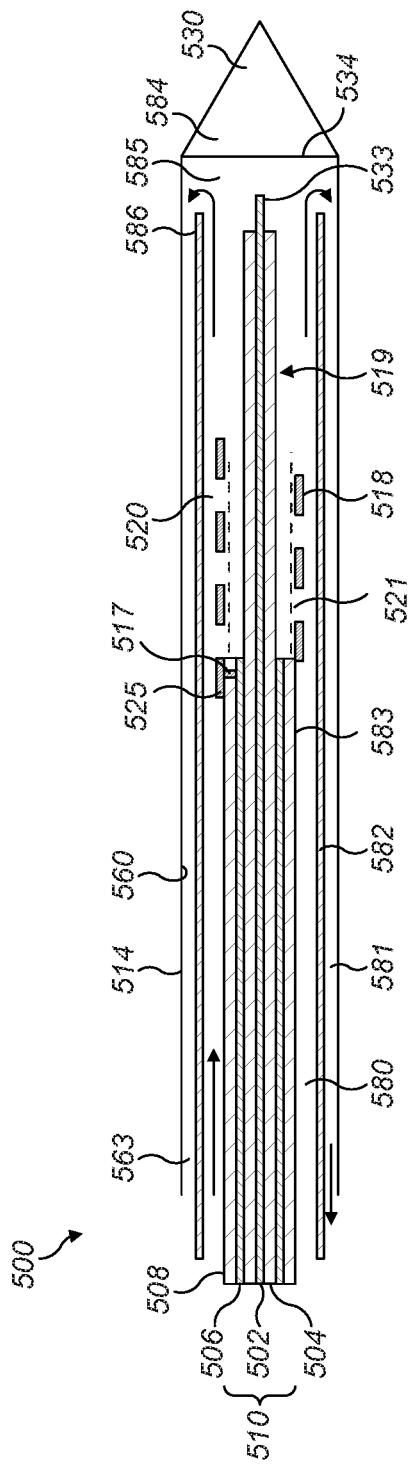
FIG. 5B is a simplified sectional view of a microwave tissue ablation device having an alternative cooling system according to one embodiment of the disclosure.
Figure 5C:
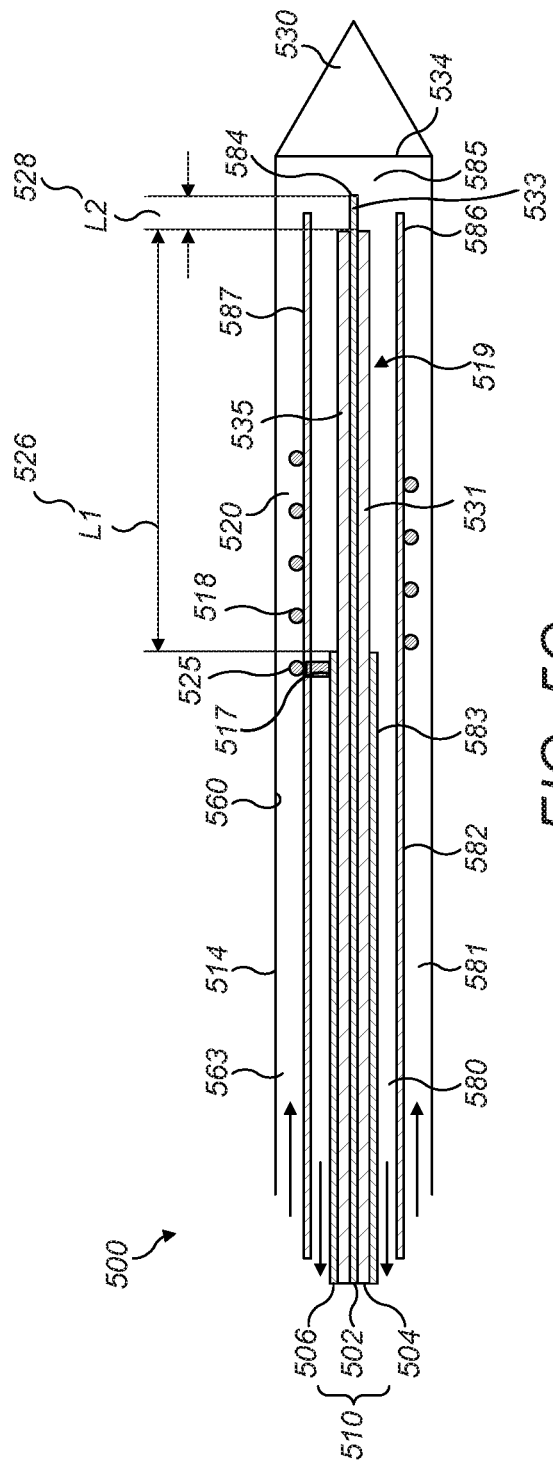
FIG. 5C is a simplified sectional view of a microwave tissue ablation device having a further alternative cooling system according to one embodiment of the disclosure.
Figure 5D:
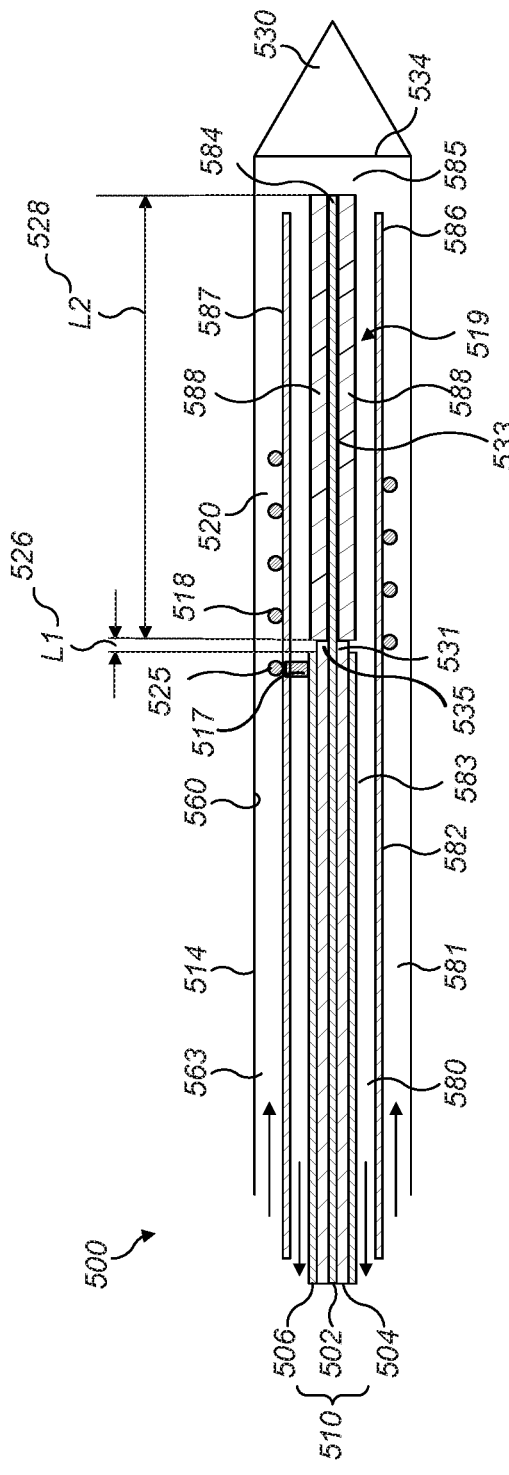
FIG. 5D is a simplified sectional view of a microwave tissue ablation device having an alternative antenna design according to one embodiment of the disclosure.

FIG. 5B illustrates a further embodiment of an ablation device according to the invention. The device illustrated in FIG. 5B 500, includes a coaxial feedline 510 with components as described for FIG. 5A including an inner conductor 502, a first insulator 504 disposed concentrically about the inner conductor 502, an outer conductor 506 disposed concentrically about the first insulator 504. The feedline illustrated has no outer insulation and is in contact with the cooling fluid in use.

The device includes an asymmetric dipole antenna 520 having a helical arm 518, formed, of a metallic ribbon. The proximal end of the helical arm 518 forms an electrical connection with the outer conductor 506 of the feedline 510 at a junction point 517. The helical arm 518 extends distally from the junction point 517 in a series of helical turns.

The antenna 520 also includes a linear arm 519. The linear arm 519 is electrically connected (integrally or otherwise) to the inner conductor 502 of the feedline 510. The linear arm 519 extends distally from a distal end of the inner conductor 502 and includes a first portion 531 surrounded by a dielectric 535, and a second portion 533 lacking dielectric. The first portion 531 of the linear arm 519 has a length L1 526. The second portion 533 of the linear arm 519 has a length L2 528. The linear arm 519 has a length of L1 plus L2. In the design of the linear arm 519 shown in FIG. 5B, L1 is much greater than L2. The helical arm 518 extends distally from the junction point 517 in a series of turns about the linear arm 519, such that the linear arm 519 extends through the helical arm 518. The helical arm 518 may be coaxial with the linear arm 519. The linear arm 519 may extend through the majority of the helical arm 518, distal to the junction 517 at the proximal end 525 of the helical arm 518. Accordingly, the majority of the helical arm 518 does not surround the outer conductor 506 or the second insulator 508. The outer conductor 506 and the second insulator 508 may not extend past or much past the junction 517 at the proximal end 525 of the helical arm 518. The outer conductor 506 and the second insulator 508 may extend only through a minority of the helical arm 518. The helical arm may not surround the feedline and/or the outer conductor by more than two complete turns of the helical arm or less than one complete turn. Alternatively, the helical arm may not surround the feedline and/or the outer conductor by more than 2 mm or less, or 1 mm or less, or 0.5 mm or less. The helical arm 518 is located proximally to the second portion 533, such that the helical arm extends about only the first portion 531. The helical arm 518 may extend about the first portion 531 but may have a diameter greater than the first portion 531, thereby creating a separation distance therebetween. The helical arm 518 may be self-supporting, or it may be supported on its inner surface or its outer surface. In FIG. 5C, the helical arm 518 is physically supported on its inner surface via a support substrate 521. The helical arm 518 forms no other electrical contact with the inner conductor 502 or the outer conductor 506, except the junction point 517. The linear arm does not touch the applicator cap 530.

FIG. 5B is illustrative of general features of a further type of cooling arrangement, applicable to arrangements of antennas described herein.

A cooling chamber 563 may surround the feedline 583 and the antenna 520. The cooling chamber as elsewhere herein may be defined between the inner wall 560 of the shaft 514, and the antenna 520 and feedline 583 and the base 534 of the applicator cap 530. The device may comprise a cooling tube 582, coaxial with the feedline 510 and antenna 520 and extending distally to a point towards the end of the linear arm of the antenna 584. The cooling tube 582 may divide the cooling chamber 563 into a first cooling conduit 580, coaxial with a distal portion of the feedline 583, which in this case extends over the helical arm 518 and the linear arm 519 of the antenna 520; and a second cooling conduit coaxial with the first extending between the outer wall of the cooling tube 582 and the inner wall 560 of the sheath 514. The cooling tube 582 and the first and second conduits are open at the distal end and may allow the cooling fluid to circulate through a cooling fluid mixing chamber 585 between the base 534 of the applicator cap 530 and the distal end of the cooling tube 582. The first and second cooling conduits co-operate to provide coolant circulation over the antenna. The first cooling conduit may be the coolant inflow and the second the coolant outflow or vice versa. This arrangement of cooling conduits allows the antenna to be cooled to the tip.

FIG. 5C illustrates a further embodiment of an ablation device according to the design. The device illustrated in FIG. 5C 500, includes a coaxial feedline 510 with components as described for FIG. 5A including an inner conductor 502, a first insulator 504 disposed concentrically about the inner conductor 502, an outer conductor 506 disposed concentrically about the first insulator 504. Feedlines may have no outer insulation and may be in contact with the cooling fluid in use.

The device includes an asymmetric dipole antenna 520 having a helical arm 518, formed, of a metallic wire, although other forms, such as a ribbon, are also possible. The proximal end of the helical arm 518 forms an electrical connection with the outer conductor 506 of the feedline 510 at a junction point 517 as described elsewhere herein. The helical arm 518 extends distally from the junction point 517 in a series of helical turns.

The antenna 520 also includes a linear arm 519. The linear arm 519 is electrically connected to the inner conductor 502 of the feedline 510. The linear arm may be, as illustrated here, an extension of the inner conductor of the feedline 510 and the dielectric may be an extension of the dielectric of the feedline. The linear arm 519 extends distally from a distal end of the inner conductor 502 and includes a first portion 531 surrounded by dielectric 535, and a second portion 533 lacking dielectric. The first portion 531 of the linear arm 519 has a length L1 526. The second portion 533 of the linear arm 519 has a length L2 528. The linear arm 519 has a length of L1 plus L2. In the design of the linear arm 519 shown in FIG. 5C, L1 is much greater than L2. As described generally for other antennas, the helical arm 518 extends distally from the junction point 517 in a series of turns about the linear arm 519, such that the linear arm 519 extends through the helical arm 518. The helical arm 518 may be coaxial with the linear arm 519. The linear arm 519 may extend through the majority of the helical arm 518, distal to the junction 517 at the proximal end 525 of the helical arm 518. Accordingly, the majority of the helical arm 518 does not surround the outer conductor 506 or the second insulator 508. The outer conductor 506 and the second insulator 508 may not extend past or much past the junction 517 at the proximal end 525 of the helical arm 518. The helical arm may not surround the feedline and/or the outer conductor by more than two complete turns of the helical arm or less than one complete turn. Alternatively, the helical arm may not surround the feedline and/or the outer conductor by more than 2 mm or less, or 1 mm or less, or 0.5 mm or less. The outer conductor 506 and the second insulator 508 may extend only through a minority of the helical arm 518. The helical arm 518 is located proximally to the second portion 533, such that the helical arm extends about the first portion 531. The helical arm 518 may extend about the first portion 531 but may have a diameter greater than the first portion 531, thereby creating a separation distance therebetween. The helical arm 518 forms no other electrical contact with the inner conductor 502 or the outer conductor 506, except the junction point 517. The linear arm does not touch the applicator cap 530.

FIG. 5C is illustrative of general features of yet a further type of cooling arrangement, applicable to arrangements of antennas described herein.

A cooling chamber 563 may surround the feedline 583 and the antenna 520 as described elsewhere herein. The cooling chamber may be defined between the inner wall 560 of the shaft 514, and the antenna 520 and feedline 583 and the base 534 of the applicator cap 530. The device may also comprises a cooling tube 582, coaxial with the feedline 510 and the linear arm of the antenna 519 and extending distally to a point towards the end of the linear arm 584. The cooling tube 582 divides the cooling chamber 563 into a first cooling conduit 580, coaxial with a distal portion of the feedline and the linear arm 519 of the antenna 520; and a second cooling conduit 581 coaxial with the first and extending between the outer wall of the cooling tube 582 and the inner wall 560 of the sheath 514. The cooling tube 582 may provide, as illustrated here, a support for the helical arm 518 of the antenna, which may be wound about the outside of the cooling tube 582. A connection may be made 517 between the proximal end of the helical arm 525 and the distal most end of the outer conductor of the feedline 583, passing through the cooling tube 582. The helical arm 518 of the antenna may thus be disposed in the second cooling conduit 581 whilst the linear arm is disposed within the first cooling conduit 580.

The cooling tube 582 and the first and second conduits are open at the distal end and may allow the cooling fluid to circulate through a cooling fluid mixing chamber 585 between the base 534 of the applicator cap 530 and the distal end of the cooling tube 582. The first and second cooling conduits co-operate to provide coolant circulation over the antenna. The first cooling conduit may be the coolant inflow and the second the coolant outflow or vice versa. This arrangement of cooling conduits also allows the antenna to be cooled to the tip and allows the helical arm to be disposed radially outward of the linear arm without providing additional support structures.

FIG. 5D illustrates a yet further embodiment of an ablation device according to the invention. The design in FIG. 5D is similar to the design described herein relative to FIG. 5C, with the only differences described hereinafter relative to the linear arm 519.

Thus, a further arrangement of the linear arm of the antenna will now be discussed with reference to FIG. 5D. As described elsewhere herein, the linear arm 519 may include a first portion 531 surrounded by a dielectric, and a second portion 533 lacking dielectric. The first portion 531 of the linear arm 519 has a length L1 526. The second portion 533 of the linear arm 519 has a length L2 528. The linear arm 519 overall, thus has a length of L1 plus L2. In contrast to previously discussed embodiments of the linear arm, in which L1 was greater than L2, in the antenna embodiment illustrated in FIG. 5D, L2 is much greater than L1. In addition, in contrast to the design shown in FIG. 5C, the second portion 533 of the linear arm 519 in FIG. 5D may have a greater diameter. For example the diameter may be greater than the diameter of the inner conductor of the feedline, or greater than the diameter of the dielectric of the first portion, or it may be the same diameter or about the same diameter as the feedline, or greater. In one aspect of the design, the diameter of the second portion 533 extends to about the same extent as the diameter of the outer conductor 506 of the feedline 510. In one approach, the second portion 533 may comprise an outer, conductive sleeve 588 surrounding and encapsulating an extension of the central conductor of the feedline 583 and electrically connected thereto. Instead of encapsulating the conductor of the feedline 583, the conductive sleeve 588 may be integral with the inner conductor of the feedline 583. The conductive sleeve 588 may be formed of the same conductive material as the inner conductor of the feedline 583.

Although, in this arrangement, the linear arm second portion 533 and the outer conductor 506 may be adjacent to each other, they are not in conductive communication. The linear arm second portion 533 and the outer conductor may be separated by the distance L1 526, the length of the linear arm first portion 531. Moreover, the dielectric 535 surrounding the conductor of the first portion 531 may electrically insulate the second portion from the outer conductor 506.

Where the second portion is larger than the first portion, the first portion may be for example 0.1 to 2 mm in length.

Where the second portion 533 is longer than the first 531, the helical arm typically extends distally over both the first portion 531 and also at least a proximal portion of the second portion 533.

General dimensions for the various portion of the antenna are as follows. The helical arm may have an overall length of the helical arm (Lha) from 1 to 18 mm, and in particular, the helical arm ranges from 4 to 10 mm. In a particular embodiment, the helical arm ranges from 4 to 7 mm.

The linear arm of antennas herein may have a length (L1a) of from 4 mm to 14 mm and optionally from 8 mm to 10 mm. In aspects where the length L1 is much greater than the length L2, the second portion of the linear arm may have a length L2 of from 0.1 mm to 2 mm, and possibly just from 0.3 mm to 0.5 mm, the remainder of the length L1a of the linear arm being the length of the first portion, L1. In another aspect of the antenna, such as the design shown in FIG. 5D, the length L2 is much greater than the length L1 in which case the dimensions of L1 and L2 may be reversed (e.g., the unexposed portion in FIG. 5D has a length L1 of from 0.1 mm to 2 mm, and possibly just from 0.3 mm to 0.5 mm). In another aspect of the design, the exposed portion of the linear arm in FIG. 5D has a length of between 9 mm and 11 mm.

FIG. 6 shows a schematic view of the distal portion of a microwave tissue ablation device and illustrates four embodiments of the metal cap and the relationship between the distal end of the antenna and the cap 602.

Figure 6B:
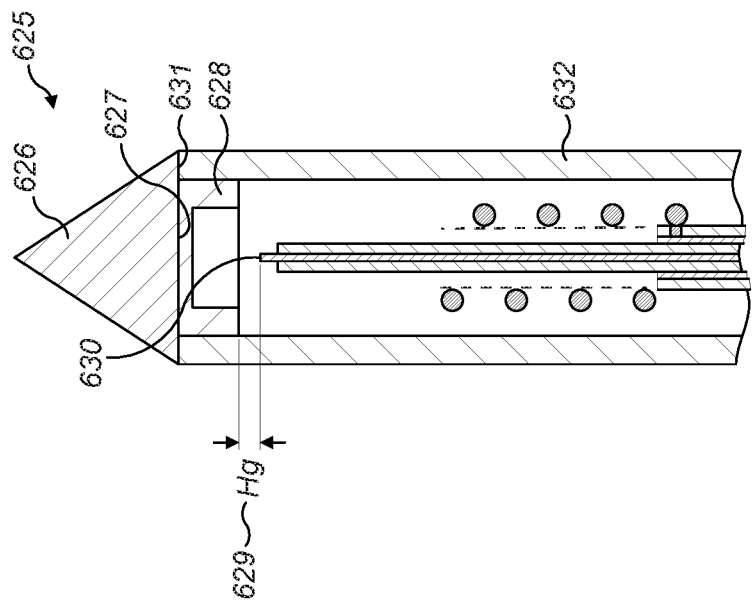
FIG. 6B is a schematic view of a microwave tissue ablation device with a metal cap according to one embodiment of the invention.
Figure 6A:
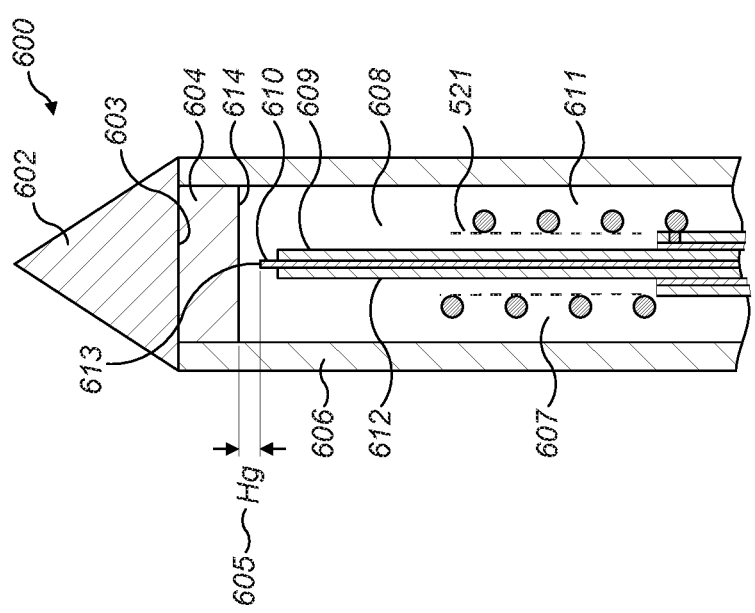
FIG. 6A is a schematic view of a microwave tissue ablation device with a metal cap according to one embodiment of the invention.

FIG. 6A shows a schematic view of a microwave tissue ablation device 600 with a metal cap 602 according to one embodiment of the invention. The metal cap 602 is conical and has a circular base 603. A solid-cylinder protrusion 604 subtends from the base 603 and has base 614, the cap has a shoulder 605 allowing the cap 602 to be inserted into the distal end of the device shaft 606 which may be metallic or ceramic. The cap may be fixed to the shaft by an adhesive (not shown). The microwave tissue ablation device 600 further includes an asymmetric dipole antenna 607 shown in simple form here and discussed in detail elsewhere herein. The antenna comprises a helical arm 611 and a linear arm 608. The linear arm having a proximal portion 609 surrounded by a dielectric 612 and a free distal portion 610 having no dielectric. The distal portion of the linear arm 608 has a tip 613 which is separated from the cap by a distance Hg. Adjusting the distance between the tip 613 and the cap alters the degree to which the metallic cap is electromagnetically coupled to the antenna, which changes the shape of the energy emission field and hence the shape of the ablation zone.

FIG. 6B illustrates a further embodiment. The microwave tissue ablation device 625 includes a metal cap which is conical and has a circular base 626. The metal cap 625 includes a base 627 from which subtends a hollow-cylinder protrusion 628. The cap has a shoulder 631 allowing the cap 626 to be inserted into the distal end of the device shaft 632. The cap may be fixed to the shaft by an adhesive (not shown). The microwave tissue ablation device 625 further includes an asymmetric dipole antenna 629 with features as described in FIG. 6A.

As shown in FIG. 6B, a gap HG 629 is disposed between the proximal end of the hollow-cylinder protrusion 628 and the distal end of the asymmetrical dipole antenna 630.

FIG. 6C is a schematic view of a microwave tissue ablation device 635 with a metal cap 636 according to one embodiment of the invention. The metal cap 636 is a circular based cone having a base 637. The microwave tissue ablation device 625 further includes an asymmetric dipole antenna 639 with features as described in FIG. 6A.

The metallic cap 636 is affixed directly to the distal end 640 of the device shaft 641. The distal tip of the linear arm of the antenna 639 is a distance Hg 638 away from the base of the cap 636. The gap Hg 638 is axially disposed between the proximal end of base 637 and the distal end of the asymmetric dipole antenna 639.

FIG. 6D is a schematic view of a microwave tissue ablation device 645 with a metal cap 646 according to one embodiment of the invention. The metal cap 677 is conical and has a circular base 648. A cylindrical protrusion 649 subtends from center of the circular base 647 leaving a shoulder 648 which allows the cylindrical protrusion to be inserted into the distal end of the device shaft 655. A blind ending cylindrical void or pocket 650 is formed centrally on the base of the cylindrical protrusion and is configured to accept a length Hp 659 of the distal portion 652 of the linear arm of the antenna which is axially and radially spaced from the walls 658 of the void 650.

Other features of the antenna are as described in FIG. 6A.

Figure 7A:
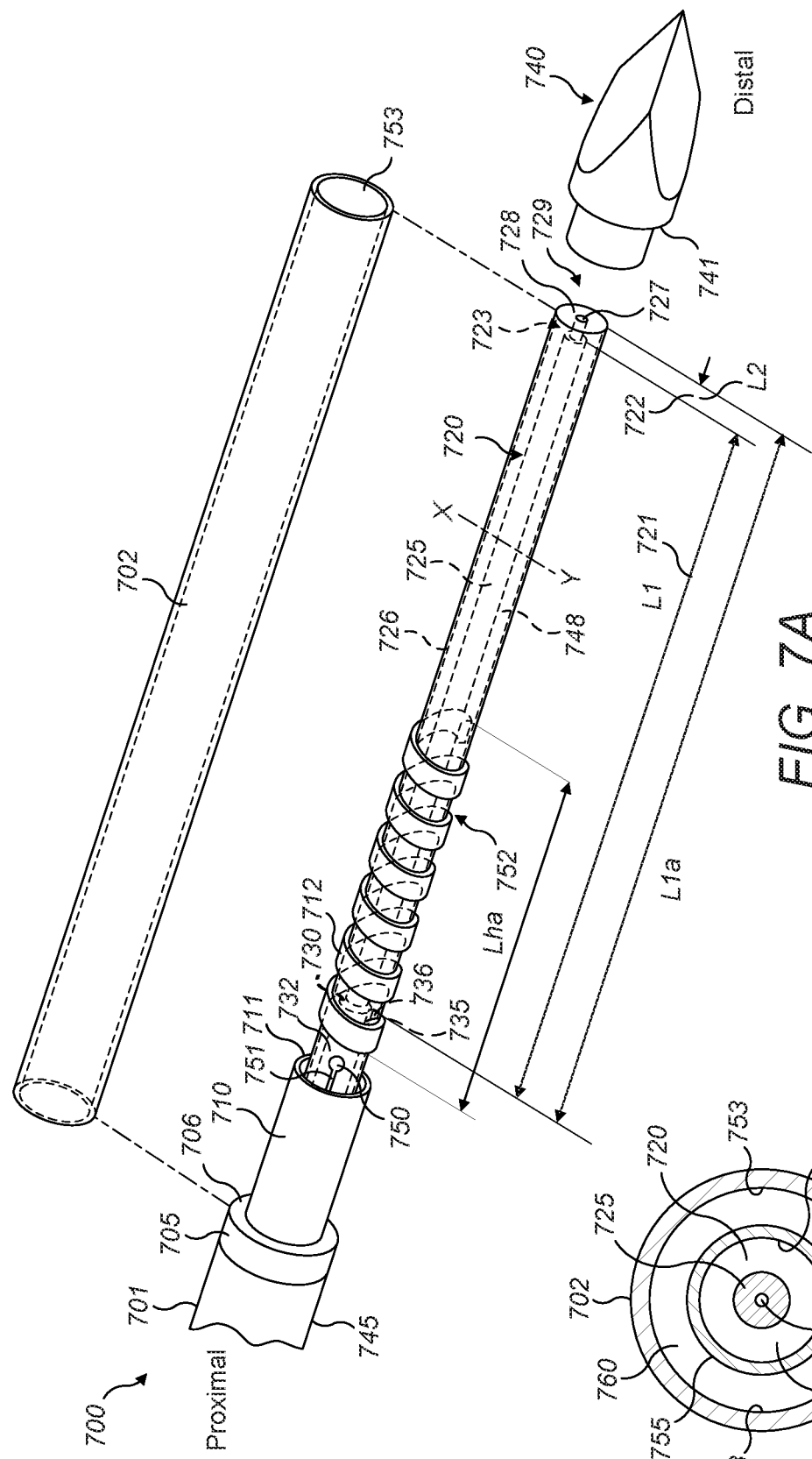
FIG. 7A is a perspective view of a microwave tissue ablation device according to one embodiment of the disclosure.
Figure 7B:
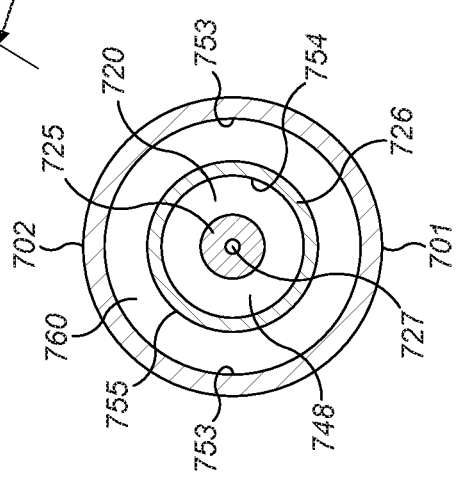
FIG. 7B is a sectional schematic view of a microwave tissue ablation device according to one embodiment of the disclosure. The section is taken through X-Y of FIG. 7A.

FIGS. 7A and 7B are illustrative of several features of the device. FIG. 7A is a perspective view of a microwave tissue ablation device 700 according to one embodiment of the disclosure. FIG. 7B is a sectional view across the line XY to illustrate one embodiment of the cooling features.

The tissue ablation device 700 of FIG. 7A, has a shaft 701 surrounding and typically co-axial with both the microwave antenna and at least a portion of the feedline. The shaft typically extends from a proximal manifold to a distal cap. Both the antenna and the feedline are disposed within the shaft. The shaft may be of unitary construction or it may have a metal portion 745 and a non-metallic portion such as a ceramic portion 702 as shown in the figure. Where present, the non-metallic portion may extend axially to be at least co-extensive with the antenna. In FIG. 7A the ceramic portion extends from distal end 706 of a collar 705 to the base 741 of the cap 740. The non-metallic portion 702 is shown displaced separately from the shaft 701, in order to show the internal features of the device.

As illustrated, the tissue ablation device 700 may include a resilient element 705 (e.g., as described in more detail elsewhere herein, and an adaptor 710 to join the metal portion 745 to the ceramic portion 702 of the shaft. In devices of the invention, an adaptor may be used to take up any difference in shaft thickness between the two portions and additionally may act to reduce flexing between the metal shaft 745 and the ceramic portion 702. In devices of the invention, a resilient annular spacer such as 705 between the ceramic portion and the metal portion of the shaft as shown here, act to provide resilience to this region and so reduce the occurrence of fractures at this point due to strain on the shaft during use. The tissue ablation device 700 may include a temperature sensor 750 for example, housed next to the internal adaptor 710, having an electrical connection 751 via the manifold to the control unit.

As described, for example, with respect to FIG. 1, microwave energy generated by a microwave generator can be supplied to the antenna by a power cable which electrically connects the microwave generator to the feedline 732 of the antenna 752 within the device 700. The microwave ablation devices also have a shaft surrounding and typically co-axial with both the microwave antenna and at least a portion of the feedline. The shaft typically extends from a proximal manifold to a distal cap.

The feedline may comprise an inner conductor, an outer conductor and a dielectric disposed there-between. The feedline may comprise a further dielectric or insulator which insulates the outer conductor from other parts of the device and acts as an outer insulator to the feedline, but it is not required in all embodiments. In some embodiments the further dielectric may be absent from the distal portion of the feedline, at least up to the junction point. The feedline may lack such a further dielectric within the device shaft, such as between a proximal feedline connector of a distal manifold, and the junction point of the antenna. The feedline is typically a co-axial cable having a central conductor, surrounded by a first dielectric, or insulator, the first dielectric being surrounded by the second conductor, which may be covered by the further dielectric or insulator as described above. The inner conductor is typically the power conductor.

Referring to FIG. 7A, A tissue ablation device 700 has an antenna 752 including a helical arm 712, and a linear arm 720. A proximal end 735 of the helical arm 712 forms an electrical connection with the outer conductor 730 of the feedline 732 at a junction point 736 and extends distally from the junction point 736. The helical arm 712 forms no other electrical contact with the inner conductor 727 or the outer conductor 730, except the junction point 736

The junction point is conveniently towards, or at, the distal most end of the feedline 732. The feedline 732 may extend beyond the junction point 736 in order to provide suitable mechanical support to the electrical junction, as described elsewhere herein. It optionally does not extend by more than 2 mm and particularly not more than 1 mm beyond the junction point 736. Alternatively it does not extend by more than 2 turns, and optionally no more than 1 turn of the helical arm.

The linear arm 720 is electrically connected to the inner conductor 727 of the feed line 732 and extends distally from the distal end of the feedline 732. The helical arm 712 is disposed coaxially about the linear arm 720.

The device has a cooling system configured to pass a coolant fluid over the antenna. The cooling system is configured to pass a coolant fluid over at least a portion of the feedline and over the antenna as described in more detail below.

As shown in FIG. 7A, the helical arm 712 may be coiled on a tube 726, which may act a s a support substrate, or as in this case, acts as a cooling tube, which may extend from the manifold (not shown), through the metal portion 745 of the shaft to the tip of the antenna 728. The electrical connection between the helical arm 712 of the antenna and the outer conductor 730 of the feedline 732 passes through the tube 726 at the junction point 736. The helical arm 712 has a length (Lha). In some examples, the overall length of the helical arm (Lha) can range from 1 to 18 mm, optionally the helical arm ranges from 4 to 10 mm. In an optional embodiment, the helical arm ranges from 4 to 7 mm.

The cooling tube 726 is disposed about the linear arm 720 of the antenna. It defines a first cooling conduit 748 between the inner wall 754 of the tube 726 and the linear arm 720 and a second cooling conduit 760 between the outer wall 755 of the tube 726 and the inner wall of the shaft 753. Coolant may be pumped through the space between the tube 726 and the linear arm 720 to a mixing chamber 729 between the tube 726 and the cap 740 and returns in the space between the outside of the tube 726 and the ceramic portion 702 of the shaft, through the space 711 between the inside of shaft and the adaptor 710 and back down the metal portion 745 of the shaft to the manifold.

The linear arm 720 is an extension of the inner conductor 727 of the feedline 732 and is surrounded by a dielectric layer 725, except for the second portion 723, which is free of dielectric.

The linear arm of the antennas described herein is a conductor which is electrically connected to the inner conductor of the feedline 732 and extends distally therefrom particularly on an axis co-axial with the helical arm and/or the feedline 732. The conductor is optionally in the form of a straight wire. In a particular embodiment, the linear arm includes a first, proximal, insulated portion and a second distal non insulated portion. Typically the first portion is surrounded by a dielectric and a second portion, distal of the first portion is free of dielectric. The second portion extends to the tip of the arm. The dielectric surrounding the first portion of the linear arm may extend from the distal end of the feedline 732. In its simplest form, the linear arm of the antenna may be an extension of the feedline's inner conductor. The dielectric may then be an extension of the dielectric disposed between the central and outer conductors of the co-axial feedline.

Optionally the linear arm and the helical arm of the antenna are co-axial with the shaft of the ablation device, and thus the linear arm is co-axial with and extends distally from, the helical arm. As shown, the linear arm 720 of the asymmetric dipole antenna of FIG. 7A has a length L1a. The linear arm includes a first portion L1 721 coated with an insulator, which may be an extension of the first dielectric layer of the feedline 732 and which may be disposed between the inner conductor 727 and the outer conductor 730 and is not visible in this view.

The linear arm 720 further includes a second portion 723 which has a length L2 722 and which is not coated with the insulator. In one embodiment, the second portion L2 722 is exposed to the circulating coolant.

As shown in FIG. 7A, the linear arm 720 extends through the helical arm 712. The helical arm 712 may be coaxial with the linear arm 720. The linear arm 720 may extend through the majority of the helical arm 712, distal to the junction 736 at the proximal end 735 of the helical arm 712. Accordingly, the majority of the helical arm 712 does not surround the outer conductor 730 or an insulator surrounding the outer conductor 730. It may not extend by more than 2 mm and particularly not more than 1 mm beyond the junction point 736. Alternatively it does not extend by more than 2 turns, and potentially no more than 1 turn of the helical arm.

The outer conductor 730 and the insulator surrounding the outer conductor 730 may not extend past or much past the junction 736 at the proximal end 735 of the helical arm 712. The outer conductor 730 and the insulator surrounding the outer conductor 730 may extend only through a minority of the helical arm 712.

In one embodiment the helical arm 712 is disposed proximally to the second portion of the linear arm L2 723, such that the helical arm 712 extends about the only the first portion of the linear arm L1 721. In a second approach the helical arm may extend over the whole of the first portion and optionally also over at least the proximal portion of the second part of the linear arm as discussed under FIG. 5D.

In one aspect, L2, the portion of the linear arm lacking dielectric, is partially or completely inserted into the metal cap but does not touch the cap. This can be achieved by creating an open pocket in the base of the cap into which this part of the antenna or a portion of it is inserted. The degree to which the exposed distal tip is inserted influences the shape of the distal portion of the energy field and hence the shape of the ablation zone.

Where the distance between the tip and cap is greater than 3 mm they are not considered to be sufficiently coupled to be useful in shaping the ablation, particularly at 2.45 GHz.

In general the linear arm of antennas herein, 720 may have a length (L1a) of from 4 mm to 14 mm and possibly just from 8 mm to 10 mm. In one aspect of the antenna design, such as the design shown in FIG. 7A, the length L1 is much greater than the length L2. In such designs, the exposed portion 723 of the linear arm has a length L2 of from 0.1 mm to 2 mm, and possibly just from 0.3 mm to 0.5 mm, the remainder of the length L1a of the linear arm 720 being the length L1 of the first portion 721. In another aspect of the antenna design, such as the design shown in FIG. 5D, the length L2 is much greater than the length L1. In this aspect, the dimensions of L1 and L2 may be reversed (e.g., the unexposed portion in FIG. 5D has a length L1 of from 0.1 mm to 2 mm, and possibly just from 0.3 mm to 0.5 mm). In another aspect of the design, the exposed portion of the linear arm of the approach of FIG. 5D has a length of between 9 mm and 11 mm.

Helical arms may have a length Lha of 1 to 18 mm and comprises 1 to 14 turns, alternatively 4 to 10 mm and 4 to 8 turns or 4 to 6 mm and comprise 3 to 5 turns.

Thus in an optional embodiment, the helical arm 712 of the antenna is in the form of a ribbon, and may have a length (Lha) of 1 to 18 mm and comprises 1 to 14 turns, the linear arm 720 of the antenna is 4 to 14 mm long and has a second, distal portion 723 lacking dielectric of 0.1 to 3 mm mm long. The portion lacking dielectric may be separated from the base of a cap by 0.2 to 3 mm.

In a more specific aspect of the design, the helical 712 arm of the antenna is in the form of a ribbon, having a length (Lha) of 4 to 10 mm and comprises 4 to 8 turns, the linear arm 720 of the antenna is 7 to 10 mm long and has a second, distal portion 723 lacking dielectric of 0.3 to 0.5 mm long. The portion lacking dielectric may be separated from the base of a cap by 1 to 2 mm.

In an even more specific aspect of the design, the helical arm 712 of the antenna is in the form of a ribbon, having a length (Lha) of 4 to 6 mm and comprises between 3 to 5 turns. The linear arm 720 is 7 to 10 mm long having a second, distal portion 723 lacking dielectric 0.3 to 0.5 mm long. The portion lacking dielectric may be separated from the base of a cap by 1 to 2 mm, optionally by at or about 1.5 mm.

Where the shaft has a non-metallic portion (e.g., ceramic portion 702), the non-metallic portion may extend axially to cover the antenna and thus is at least co extensive with the radiating portion of the antenna. In one embodiment the non-metallic portion extends at least from the proximal most point of the helical arm to the distal end of the shaft. (e.g., the point of attachment of the tip of the device). The non-metallic portion extends axially and circumferentially such that the shaft may be non-metallic between the proximal and distal extent of the non-metallic portion.

A cap may be configured to seal the distal end of the device to prevent coolant leakage or tissue fluid penetration. The cap may be manufactured as a separate part and may be configured to be attached to the shaft. The cap may be configured to aid insertion into tissues and to penetrate the skin of a patient and so may, for example, come to a distal point, or be configured as a trocar. The cap 740 shown in FIG. 7 includes a trocar tip. The trocar tip of cap 740 can be made with stainless steel and/or ceramic.

In some examples, the cap may be made of any suitable biocompatible material such as a biocompatible polymer, composite, ceramic or metal such as stainless steel. Where the cap is metal, the cap and the distal end of the antenna (i.e. the distal end of the linear arm of the antenna) may be configured, to be electromagnetically coupled. This can be done by adjusting the distance between the distal tip of the antenna and the cap so that they become electromagnetically coupled at the frequency and at the power at which the antenna is intended to operate. This effect can be used to tune the shape of the distal portion of the energy field generated by the antenna and hence the shape of the ablation zone. The cap and antenna need not, however be so coupled, i.e. the antenna may be electromagnetically decoupled from the cap. In one embodiment, the tip and cap do not touch. In practice the gap between the tip and the cap is 0.2 mm or greater, particularly 0.2 mm to 3 mm and most particularly 1 to 2 mm. Most particularly is at or about 1.5 mm.

The shape of the energy field and hence the ablation volume can also be influenced by the provision of a metallic sheath concentric with the feedline. The sheath may be cylindrical and extends over at least a portion of the feedline proximal to the antenna. The sheath may also extend over at least a portion of the antenna, but optionally it terminates at a point proximal to the distal most point of the helical arm of the antenna and does not extend over the antenna. Optionally the gap between the sheath and the distal most portion of the helical arm is at least 0.1 mm. The gap may be for example, between 0.1 to 2 mm or between 0.1 to 1 mm, or it is about 0.5 mm. The sheath may not be placed on the outer surface of the shaft, but is radially displaced from the feed line and co axial with it. It may be placed between the feedline and the inner wall of the shaft. In one arrangement, the metal sheath may be an adaptor sleeve as described elsewhere herein.

Optionally, a coolant chamber is defined between the inner walls of the device shaft. The chamber may be bounded distally by the cap and may be bound proximally by one or more proximal seals, or stoppers which close the coolant chamber proximally. They are optionally formed at the manifold or at a point between the manifold and the proximal portion of the helical arm of the antenna. The cooling system comprises at least one coolant inlet conduit configured to deliver coolant to the coolant chamber and at least one coolant outlet conduits to remove coolant from the chamber. The coolant inlet and coolant outlet conduits may pass through the proximal seals/stoppers. In one approach, the coolant inlet conduit is a coolant inlet tube configured to deliver coolant to a position adjacent to and radially outward of the antenna and or feedline. In this case, the coolant inlet tube may be disposed within the coolant chamber between the antenna and the inner wall of the shaft. Optionally it is displaced radially outward of the feedline.

The cooling system may additionally comprise a coolant mixing chamber in fluid communication with both the coolant inlet and coolant outlet conduits, such that the coolant inlet and coolant outlet are in fluid communication via the coolant mixing chamber. The coolant mixing chamber may be configured to allow coolant to pass over at least a portion of the antenna, particularly at least a portion of the linear arm of the antenna. The coolant mixing chamber is particularly configured to allow coolant to pass over the distal portion of the linear arm of the antenna and at least a portion of the cap.

In an alternative embodiment, the cooling system comprises a coolant chamber defined between the inner walls of the device shaft. The chamber may be bounded distally by the cap and may be bounded proximally by a seal between the manifold and the shaft, or at some point distal from the manifold and between the antenna and the manifold as previously described. The coolant chamber may surround the antenna and at least a distal portion of the feedline.

In an embodiment, (see for example FIG. 7A) the cooling system further comprises a cooling tube disposed about the feedline, the cooling tube may extend distally about the feedline and optionally coaxial therewith. The cooling tube optionally divides the coolant chamber into a first cooling conduit 748 and a second cooling conduit 760, the first cooling conduit disposed between the feedline and the inner wall of the cooling tube and the second cooling conduit disposed between the outer wall of the cooling tube and the inner wall of the device shaft. The cooling tube optionally extends over the distal portion of the feedline and extends distally about at least a portion of the antenna, optionally the cooling tube extends at least to the tip of the linear arm of the antenna. A variety of materials are suitable for the cooling tube, but it may be non-metallic. Conveniently the cooling tube may be made of a thermoset polymer such as a polyimide or of a thermoplastic polymer resin such as polyethylene terephthalate (PET) or a fluoropolymer such as polytetrafluroethylene (PTFE), or of a PAEK such as PEEK.

As described elsewhere herein, in the example of FIG. 7A, the helical arm may be coiled on a tube 726. In an embodiment, the tube may be the cooling tube 726 which defines a first cooling conduit 748 between the inner wall 754 of the tube 726 and the feedline 732 and a second cooling conduit 760 between the outer wall 755 of the tube 726 and the inner wall of the shaft 753. Coolant may be pumped through the space between the tube 726 and the feedline 732 a mixing chamber 729 between the tube 726 and the cap 740 and returns in the space between the outside of the tube 726 and the ceramic portion of the shaft, through the space 711 between the inside of shaft and the adaptor 710 and back down the metal portion 745 of the shaft to the manifold.

The helical arm of the antenna may be disposed within the first cooling conduit or within the second cooling conduit. For example in one embodiment, the device may comprise an antenna support disposed co axially about the linear arm (as shown in FIG. 5B). The helical arm of the antenna may be supported on the antenna support, for example supported on the inner face of the support or the outer face of the support. The antenna support may be disposed radially outward of the linear arm, but radially inward of the cooling tube. The helical arm will therefore be disposed in the first cooling conduit. In this case, the cooling tube may extend to cover a portion of the helical arm, and optionally to cover the helical arm and a portion of the linear arm, but most particularly the cooling tube extends at least to the distal end of the antenna, such that the first cooling conduit extends at least to the tip of the antenna.

Otherwise the cooling tube extends to cover the distal portion of the feedline and at least a proximal portion of the linear arm, but most particularly the cooling tube extends at least to the distal end of the linear arm, such that the first cooling conduit extends at least to the tip of the antenna. The helical arm may then be wound about the cooling tube such that the helical arm is disposed in the second cooling conduit.

This cooling system may additionally also comprise a coolant mixing chamber in fluid communication with both the first cooling conduit and the second cooling conduit, such that the first cooling conduit and the second coolant are in fluid communication via the coolant mixing chamber. The coolant mixing chamber may be configured to allow coolant to contact a portion of the cap.

Either the first or the second cooling conduit may act as the coolant input conduit or coolant output conduit. The first and second cooling conduits are open at the distal end allowing the coolant to circulate through the coolant mixing chamber between the distal end of the cooling tube and the base of an applicator cap.

The cooling tube optionally extends proximally towards the manifold. The first cooling conduit and second cooling conduits are in fluid communication with coolant input and output connectors of the manifold, for the supply of coolant and discharge of coolant during use.

In a particular approach, the helical arm of the antenna, optionally in the form of a ribbon, is wound about the cooling tube. In this case, the helical arm is in electrical contact with the outer conductor of the feedline at the junction point and extends distally in a series of turns about the cooling tube as described above. In this case, the cooling tube optionally extends distally at least to the junction point of the antenna and feedline, optionally it extends, further, to cover at least a portion of the linear arm, but most particularly the cooling tube extends to the tip of the linear arm, such that the first cooling conduit extends at least to the tip of the antenna. Optionally the electrical contact between the distal end of the helical arm and the outer conductor of the feedline passes through the cooling tube.

In this approach it is optional that the outer insulator does not extend over the distal portion of the feedline. Optionally it does not extend over at least the portion which extends from a point on the feedline immediately proximal of the helical arm of the antenna to the junction point. The outer insulator may be absent from the entire feedline within the shaft of the ablation device.

In embodiments in which the cooling system comprises a cooling tube as described above, the helical arm may be either a wire or a ribbon, but is most particularly a ribbon. The helical arm may be in the form of a cylindrical conductor, having a helical gap running from its proximal end to its distal end to give a helical conductor having a planar conductor surface disposed about the feedline and optionally co-axial with it.

The cooling systems described herein pass a coolant (e.g., water) over the feedline and at least a portion of the antenna, optionally the whole antenna. It is not necessary to insulate the antenna from the coolant for normal operation. In some embodiments described herein parts of the feedline are lacking an outer insulator surrounding the feedline. The feedline may be lacking insulator between the manifold and the junction point or its whole length within the device shaft. The helical arm of the antenna may also lack any insulation, particularly where it is wound about a cooling tube.

The ablation devices described herein may additionally comprise one or more temperature sensors, such as a thermocouple, to measure the temperature at points along the shaft. Typically a thermocouple may be located within the cooling system and configured to measure the temperature of the coolant or of other parts of the device such as the feedline or device shaft during operation of the device. The tissue ablation device 700 of FIG. 7A may include a temperature sensor 750 housed next to the internal adaptor 710 and having an electrical connection 751 via the manifold to the control unit.

As described elsewhere herein, ablation devices such as those described herein typically comprise a proximal manifold as discussed briefly above. The manifold typically comprises connectors for connecting the feedline to an energy supply line and for connecting electrical devices within the device shaft to control systems. Such connectors may be permanent or demountable. The manifold may also comprise coolant manifold with input and output connectors for connecting the coolant input to a coolant supply and the coolant output to waste or recirculating system. The manifold may also form part of a handle configured to provide a firmer grip for a surgeon to handle the tissue ablation device.

The device 700 includes a trocar tip 740. In one embodiment, the trocar tip 740 can be the applicator cap 130 shown in FIG. 5, the metal caps shown in FIGS. 6A-6D, and the trocar tip 330 shown in FIG. 3A. The trocar tip 740 can be made with stainless steel and/or ceramic.

Figure 8B:
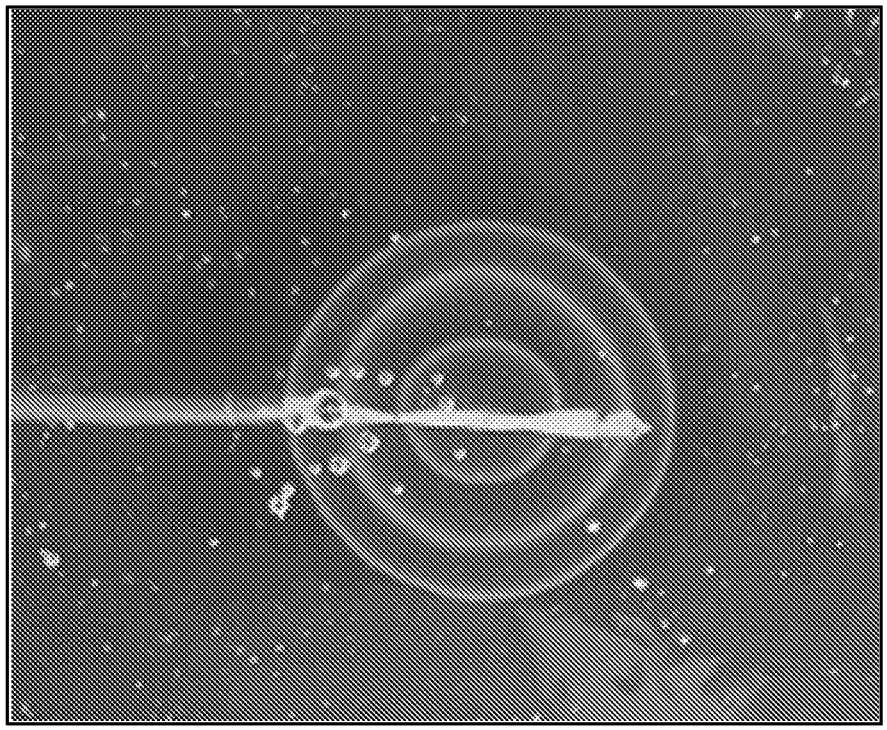
FIG. 8B is another picture showing the ablation pattern produced using an ablation device according to one embodiment of the disclosure.
Figure 8A:
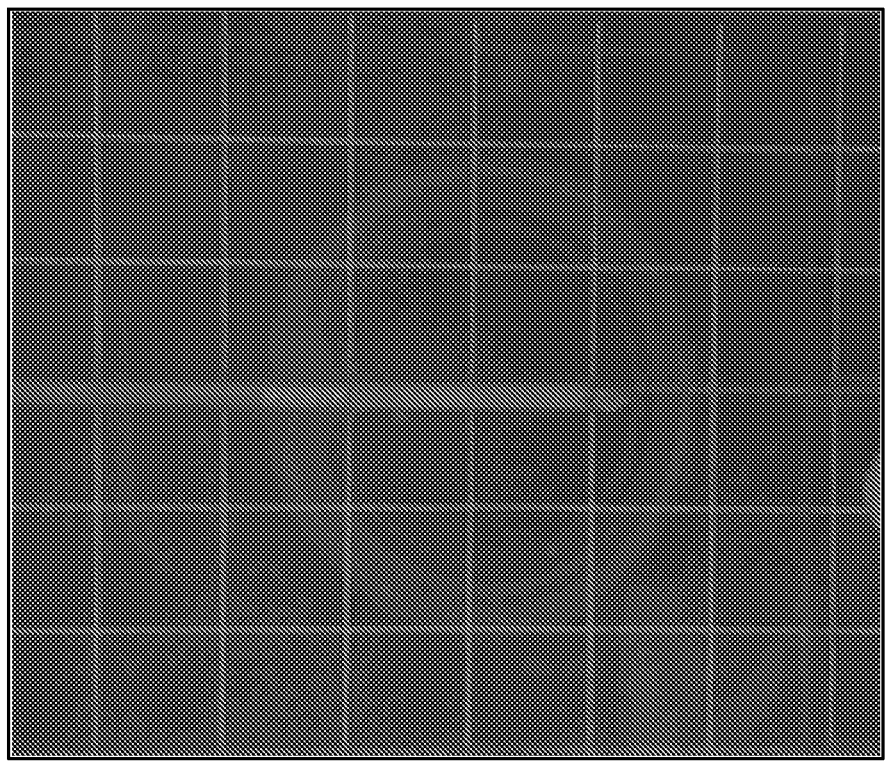
FIG. 8A is a picture showing the ablation pattern produced using an ablation device according to one embodiment of the disclosure.

FIG. 8A is a picture showing ablation effect of the tissue ablation device according to one embodiment of the disclosure. The tissue was heated for 25-30 W over 5 mins. As shown in FIG. 8A, the ablation volume is approximately spherical.

FIG. 8B is a picture showing ablation effect of the tissue ablation device according to one embodiment of the disclosure. The saline was heated for 90 W over 4 mins. As shown in FIG. 8B, the ablation volume is approximately spherical.

The invention claimed is:

1. A microwave ablation probe comprising:
   a feedline having an inner conductor, an outer conductor and a dielectric disposed therebetween;
   an asymmetric dipole antenna, the antenna including:
      a helical arm, the helical arm being electrically connected to the outer conductor of the feedline at a junction point, the helical arm extending in a distal direction from the junction point; and
      a linear arm, the linear arm being electrically connected to the inner conductor of the feedline, the linear arm extending distally from a distal end of the feedline, the helical arm coaxially disposed about the linear arm, the linear arm extending through a majority of the helical arm distal to the junction point at a proximal end of the helical arm such that the majority of the helical arm refrains from surrounding the outer conductor, the linear arm further including:
         a first portion surrounded by a dielectric, and
         a second portion free of dielectric, the second portion being distal to the first portion by a length to be a free end of the linear arm; and
   a shaft, the antenna and the feedline being disposed within the shaft such that a shape of an intended ablation zone is defined by the helical arm and linear arm and is tunable by the length of the second portion, the shaft comprising a metal portion and a ceramic portion, the ceramic portion extending axially between proximal and distal ceramic portion ends to be at least co-extensive with the antenna, the proximal and distal ceramic portion ends forming a portion of an outer surface of the shaft.

2. The microwave ablation probe of claim 1, wherein the helical arm is 1 to 14 turns.

3. The microwave ablation probe of claim 1, wherein the helical arm of the antenna is a ribbon.

4. The microwave ablation probe of claim 1, wherein the linear arm of the antenna is electromagnetically coupled to a metallic cap but is not connected to the metallic cap such that adjusting the length of the second portion corresponds to adjusting a distance between a distal tip of the antenna and the metallic cap to thereby alter a degree to which the metallic cap is electro-magnetically coupled to the antenna to thereby tune the shape of the intended ablation zone.

5. The microwave ablation probe of claim 4, wherein the distal tip of the antenna is separated from the metallic cap by a distance of 0.2 mm to 3 mm.

6. The microwave ablation probe of claim 1, wherein the antenna is configured to emit microwave radiation in a frequency band from about 2 GHz to about 6 GHz.

7. The microwave ablation probe of claim 1, further comprising a strain relief region that connects the metal portion and the ceramic portion at a joint and is configured to provide additional resilience to the joint.

8. The microwave ablation probe of claim 7, wherein the strain relief region comprises a resilient element positioned between the metal and ceramic portions of the shaft, thereby forming a spacer therebetween.

9. The microwave ablation probe of claim 1, further comprising a cooling system configured to pass a coolant fluid over the antenna.

10. The microwave ablation probe of claim 9, wherein the cooling system is at least one of:
    configured to pass a coolant fluid over at least a portion of the feedline and over the antenna;
    arranged to include a coolant chamber defined between inner walls of the shaft; and
    arranged to include a cooling tube.

11. The microwave ablation probe of claim 10, wherein the cooling tube divides the coolant chamber into a first cooling conduit and a second cooling conduit, the first cooling conduit disposed between the linear arm and inner wall of the cooling tube and the second cooling conduit disposed between an outer wall of the cooling tube and the inner walls of the shaft.

12. The microwave ablation probe of claim 11, wherein the linear arm of the antenna is disposed in the first cooling conduit and the helical arm of the antenna is disposed in the second cooling conduit.

13. The microwave ablation probe of claim 10, wherein the helical arm of the antenna is wound about the cooling tube and extends distally from the junction point in a series of turns about the cooling tube.

14. A microwave ablation needle comprising:
    a feedline electrically connected to an asymmetric dipole microwave antenna having helical and linear arms, and
    a shaft surrounding the asymmetric dipole microwave antenna and the feedline such that tuning and matching of the antenna are achievable by changing number of helical turns of the helical arm, a pitch of the helical arm, a length of the linear arm, and an exposed portion of a free distal end of the linear arm,
    wherein the shaft comprises a non-metallic portion and a metallic portion, the non-metallic portion extending axially between proximal and distal non-metallic portion ends to be co-extensive with at least a portion of the antenna that radiates microwaves, the non-metallic portion of the shaft being ceramic, the proximal and distal non-metallic portion ends forming an outer surface of the shaft.

15. The microwave ablation needle of claim 14, wherein the asymmetric dipole microwave antenna comprises:
    a helical arm, being electrically connected to an outer conductor of the feedline at a junction point, the helical arm extending in a distal direction from the junction point; and
    a linear arm, the linear arm being electrically connected to an inner conductor of the feedline, the linear arm extending distally from a distal end of the feedline, the linear arm further including
        a first portion surrounded by a dielectric; and
        a second portion free of dielectric, the second portion being distal to the first portion.

16. The microwave ablation needle of claim 14, wherein the antenna is configured to emit microwave radiation in a frequency band from about 2 GHz to about 6 GHz.

17. The microwave ablation needle of claim 14, further comprising a resilient element disposed between the non-metallic portion and the metallic portion and configured to provide resilience to a joint between the non-metallic portion and the metallic portion of the shaft.

18. The microwave ablation needle of claim 17, further comprising a strain relief region that connects the metallic portion and the non-metallic portion at a joint and is configured to provide additional resilience to the joint, the strain relief region including the resilient element to form a spacer between the metallic and non-metallic portions, the spacer extending radially outward to form a surface flush with the outer surface of the shaft.

19. A microwave ablation system comprising one or more microwave ablation probes, each microwave ablation probe comprising:
- a feedline having an inner conductor, a dielectric coaxially disposed about the inner conductor and an outer conductor coaxially disposed about the dielectric; and
- an asymmetric dipole antenna, the antenna including,
  - a helical arm, the helical arm being electrically connected to the outer conductor of the feedline at a junction point, the helical arm extending in a distal direction from the junction point; and
  - a linear arm, the linear arm being electrically connected to the inner conductor of the feedline, the linear arm extending in a distal direction from a distal end of the feedline, the linear arm extending through a majority of the helical arm distal to the junction point at a proximal end of the helical arm such that the majority of the helical arm refrains from surrounding the outer conductor,
  - the linear arm further including
    - a first portion surrounded by a dielectric, and
    - a second portion free of dielectric, the second portion being distal to the first portion by a length to be a free end of the linear arm; and
- a shaft, the antenna and the feedline being disposed within the shaft such that a shape of an intended ablation zone is defined by the helical arm and linear arm and is tunable by the length of the second portion, the shaft comprising a metal portion and a ceramic portion, the ceramic portion extending axially between proximal and distal ceramic portion ends to be at least co-extensive with the antenna, the proximal and distal ceramic portion ends forming a portion of an outer surface of the shaft:
- a power module configured to provide microwave energy to the antenna; and
- one or more power cables configured to connect the power module to each microwave antenna and to deliver microwave energy provided by the power module to the antenna for the ablation of tissue.

20. The microwave ablation system of claim 19, wherein the or each microwave ablation probe comprises a cooling system to cool the antenna and/or at least a portion of the feedline, the microwave ablation system additionally comprising a cooling system configured to deliver coolant fluid to the cooling system of the microwave ablation probe, to cool the antenna and at least a portion of the feedline.

* * * * *